US012311350B2

(12) United States Patent
Li et al.

(10) Patent No.: US 12,311,350 B2
(45) Date of Patent: May 27, 2025

(54) ALKANE CATALYTIC DEHYDROGENATION REACTION DEVICE AND CATALYST REGENERATION DEVICE

(71) Applicants: SHANGHAI SUPEZET ENGINEERING TECHNOLOGY CO., LTD., Shanghai (CN); JIANGSU BOSONG ENERGY TECHNOLOGY CO., LTD., Jiangsu (CN); HANYI SHENFEI NEW MATERIALS CO., LTD., Henan (CN); CHINA UNIVERSITY OF PETROLEUM (EAST CHINA), Shandong (CN)

(72) Inventors: Chunyi Li, Shandong (CN); Lingyun Zhang, Henan (CN); Xiaoyu Zhang, Shanghai (CN); Ying Zhang, Shanghai (CN); Kaitian Mao, Shanghai (CN); Hui Li, Shanghai (CN); Chuntian Pang, Jiangsu (CN)

(73) Assignees: SHANGHAI SUPEZET ENGINEERING TECHNOLOGY CO., LTD., Shanghai (CN); JIANGSU BOSONG ENERGY TECHNOLOGY CO., LTD., Jingjiang (CN); HANYI SHENFEI NEW MATERIALS CO., LTD., Henan (CN); CHINA UNIVERSITY OF PETROLEUM (EAST CHINA), Shandong (CN)

( * ) Notice: Subject to any disclaimer, the term of this patent is extended or adjusted under 35 U.S.C. 154(b) by 889 days.

(21) Appl. No.: 17/440,000

(22) PCT Filed: Feb. 10, 2020

(86) PCT No.: PCT/CN2020/074584
§ 371 (c)(1),
(2) Date: Sep. 16, 2021

(87) PCT Pub. No.: WO2020/186937
PCT Pub. Date: Sep. 24, 2020

(65) Prior Publication Data
US 2022/0168699 A1 Jun. 2, 2022

(30) Foreign Application Priority Data

Mar. 18, 2019 (CN) .......................... 201910201890.5
Mar. 18, 2019 (CN) .......................... 201910201900.5
(Continued)

(51) Int. Cl.
*C07C 5/333* (2006.01)
*B01J 8/00* (2006.01)
(Continued)

(52) U.S. Cl.
CPC ............. *B01J 8/0055* (2013.01); *B01J 8/004* (2013.01); *B01J 8/0065* (2013.01); *B01J 8/24* (2013.01);
(Continued)

(58) Field of Classification Search
None
See application file for complete search history.

(56) References Cited

U.S. PATENT DOCUMENTS 2,325,136 A * 7/1943 Kassel ...................... B01J 8/32
502/41
2,947,577 A * 8/1960 Van Dommelen ....... B01J 8/005
406/174
(Continued)

FOREIGN PATENT DOCUMENTS

CN 1165052 A 11/1997
CN 1319643 A 10/2001
(Continued)

OTHER PUBLICATIONS

International Search Report (PCT/ISA/210) with English translation and Written Opinion (PCT/ISA/237) mailed on Apr. 24, 2020, by the Chinese Patent Office as the International Searching Authority for International Application No. PCT/CN2020/074584.

*Primary Examiner* — Jennifer A Leung
(74) *Attorney, Agent, or Firm* — BUCHANAN, INGERSOLL & ROONEY PC

(57) ABSTRACT

Disclosed is an alkane dehydrogenation circulating device, including a reaction device and a regeneration device. The
(Continued)

reaction device includes a reactor and a reaction disengager, the reaction disengager is communicated with the reactor, and the reactor is provided with a catalyst distributor through which a catalyst is sprayed into the reactor along a direction from the peripheral wall of the reactor to the central axis of the reactor; the regeneration device includes a regenerator accommodating the catalyst and a regeneration disengager located above the regenerator.

19 Claims, 10 Drawing Sheets

(30) Foreign Application Priority Data

Mar. 18, 2019 (CN) .................. 201910201901.X
Apr. 3, 2019 (CN) .................. 201910265854.5

(51) Int. Cl.
*B01J 8/24* (2006.01)
*B01J 8/26* (2006.01)

(52) U.S. Cl.
CPC .............. *B01J 8/26* (2013.01); *C07C 5/3332* (2013.01); *B01J 2208/00752* (2013.01); *B01J 2208/00991* (2013.01)

(56) References Cited

U.S. PATENT DOCUMENTS

| | | | |
|---|---|---|---|
| 3,725,495 A | | 4/1973 | Wrisberg et al. |
| 3,799,868 A | * | 3/1974 | James .................. B01J 8/18 422/144 |
| 3,839,197 A | | 10/1974 | Greenwood et al. |
| 4,206,174 A | * | 6/1980 | Heffley .................. B04C 3/00 422/147 |
| 4,578,183 A | | 3/1986 | Chou et al. |
| 4,664,888 A | * | 5/1987 | Castagnos, Jr. ......... C10G 11/18 422/147 |
| 4,792,437 A | * | 12/1988 | Hettinger, Jr. ......... C10G 11/18 422/147 |
| 4,963,328 A | | 10/1990 | Haddad et al. |
| 2003/0021737 A1 | | 1/2003 | Tamhankar et al. |
| 2004/0069681 A1 | | 4/2004 | Peterson et al. |
| 2008/0220965 A1 | | 9/2008 | Santner et al. |
| 2010/0150788 A1 | | 6/2010 | Palmas et al. |
| 2013/0156650 A1 | | 6/2013 | Walker |
| 2016/0101396 A1 | | 4/2016 | Xu et al. |
| 2017/0210685 A1 | | 7/2017 | Simanzhenkov et al. |
| 2017/0275219 A1 | | 9/2017 | Nawaz et al. |
| 2018/0216012 A1 | | 8/2018 | Marchant et al. |
| 2018/0280909 A1 | | 10/2018 | Li et al. |
| 2019/0134590 A1 | | 5/2019 | Li et al. |

FOREIGN PATENT DOCUMENTS

| | | | | |
|---|---|---|---|---|
| CN | 2489874 Y | | 5/2002 | |
| CN | 1386584 A | | 12/2002 | |
| CN | 1496970 A | | 5/2004 | |
| CN | 101116827 A | | 2/2008 | |
| CN | 101164684 A | | 4/2008 | |
| CN | 101290117 A | | 10/2008 | |
| CN | 102234531 A | | 11/2011 | |
| CN | 102294205 A | | 12/2011 | |
| CN | 102311758 A | | 1/2012 | |
| CN | 102316985 A | | 1/2012 | |
| CN | 102463072 A | | 5/2012 | |
| CN | 102659498 A | * | 9/2012 | |
| CN | 202497866 U | | 10/2012 | |
| CN | 203408694 U | | 1/2014 | |
| CN | 104388112 A | | 3/2015 | |
| CN | 104419458 A | | 3/2015 | |
| CN | 104525278 A | | 4/2015 | |
| CN | 104549073 A | | 4/2015 | |
| CN | 204469679 U | | 7/2015 | |
| CN | 104826559 A | | 8/2015 | |
| CN | 106520172 A | | 3/2017 | |
| CN | 106890602 A | | 6/2017 | |
| CN | 206298550 U | | 7/2017 | |
| CN | 107108404 A | | 8/2017 | |
| CN | 107974285 A | | 5/2018 | |
| CN | 207463192 U | | 6/2018 | |
| CN | 207478534 U | | 6/2018 | |
| CN | 109028106 A | | 12/2018 | |
| CN | 109107615 A | | 1/2019 | |
| CN | 109232153 A | | 1/2019 | |
| CN | 109499486 A | | 3/2019 | |
| EP | 0457540 A1 | | 11/1991 | |
| EP | 3409348 A1 | | 12/2018 | |
| GB | 897796 A | | 5/1962 | |
| GB | 1528432 A | | 10/1978 | |
| WO | 2013054173 A1 | | 4/2013 | |
| WO | 2014209653 A1 | | 12/2014 | |
| WO | WO-2016182786 A1 | * | 11/2016 | ................ B01J 8/00 |

* cited by examiner

ALKANE CATALYTIC DEHYDROGENATION REACTION DEVICE AND CATALYST REGENERATION DEVICE

FIELD

The present disclosure relates to a circulation system for alkane catalytic dehydrogenation reactions, and in particular to an alkane dehydrogenation reaction device, and a catalyst regeneration device, and belongs to the field of petrochemistry.

BACKGROUND

Propylene and butene are important chemical feedstocks, and propane and butane are dehydrogenated to produce propylene and butene, which not only has high selectivity of olefins, but also can produce hydrogen by-product.

Propane and butane dehydrogenation has mature technologies in application, such as Oleflex from UOP and Catofin from ABB Lummus. The former employs a supported Pt catalyst, a moving bed reaction regeneration system, which can realize a continuous reaction and catalyst regeneration. The latter employs a supported CrOx catalyst and a fixed bed reactor, a single reactor can only be operated intermittently and five reactors in parallel are required for continuous operation of the entire device.

Alkane dehydrogenation has the following characteristics: alkane dehydrogenation is a strong endothermic reaction which needs to supply a large amount of heat for the reaction in time; the conversion rate is affected by thermodynamic equilibrium and the conversion rate decreases with the increase of the pressure; and the catalyst needs to be regenerated in time due to coking and deactivation. These characteristics determine that the circulating fluidized bed is an ideal alkane dehydrogenation reactor, because the circulating fluidized bed can realize continuous reaction regeneration, a high-temperature regenerant can directly supply heat for the reaction in time, and the pressure drop of the fluidized bed is smaller under the condition of a same linear velocity. However, in order to achieve a real technological breakthrough, the circulating fluidized bed dehydrogenation technology needs to solve the problems from the aspects of catalysts, reaction devices and catalyst regeneration devices, so as to further improve the catalytic dehydrogenation reaction process of alkanes.

SUMMARY

A first object of the present disclosure is to provide an alkane dehydrogenation circulating fluidized bed reaction device, on one hand, an alkane dehydrogenation reaction is carried out in the reaction device, which is beneficial to sufficient contact of oil gas with a catalyst, so as to promote the dehydrogenation reaction.

On the other hand, the alkane dehydrogenation circulating fluidized bed reaction device of the present disclosure increases the effect of gas-solid separation within a disengager and reduces catalyst attrition.

A second object of the present disclosure is to provide a catalyst regeneration device which can avoid the local temperature of a regenerator from being too high and reduce the production of nitrides.

A third object of the present disclosure is to provide an alkane catalytic dehydrogenation-cracking combined reaction device which is conducive to the improvement of the conversion rate of ethane and propane dehydrogenation.

The alkane dehydrogenation circulating fluidized bed reaction device of the present disclosure includes a reactor and a reaction disengager, the reaction disengager is communicated with the reactor, and a reaction feedstock inlet is formed on the reactor, and the reactor is provided with a catalyst distributor through which a catalyst is sprayed into the reactor along a direction from a peripheral wall of the reactor to a center axis of the reactor, and the reaction feedstock inlet is located below the catalyst distributor.

In the alkane dehydrogenation circulating fluidized bed reaction device according to the present disclosure, the reaction disengager is located above the reactor, an outlet of the reactor is located inside the reaction disengager, and a primary cyclone separator, a primary cyclone riser, and a cover body are arranged in a disengager section of the reaction disengager. The cover body includes an upper part and a lower part, the upper part of the cover body is a truncated cone, a lower bottom surface of the truncated cone is the lower part of the cover body, and the lower part of the cover body is a cylindrical structure; an area of an opening in a lowermost end of the cover body is greater than an area of the outlet of the reactor. A circumference of an upper base of the truncated cone is connected with a periphery of the primary cyclone riser, or the circumference of the upper base of the truncated cone is connected with a periphery of the primary cyclone above an inlet of the primary cyclone separator.

The alkane dehydrogenation circulating fluidized bed reaction device of the present disclosure includes a reactor and a disengager, and the disengager is communicated with the reactor, an outlet of the reactor is located inside the disengager. The disengager is provided with a first flow divider and a second flow divider, and both the first flow divider and the second flow divider are located above the outlet of the reactor; the first flow divider is a component for reducing a gas velocity in the upward direction of a gas flow discharged from the outlet of the reactor. The second flow divider includes a second cover body of which a cross-section area gradually decreases from bottom to top, both an uppermost end and a lowermost end of the second cover body are open. And the first flow divider is located within the second flow divider.

A reaction device for preparing alkenes by catalytic dehydrogenation-cracking of alkanes of the present disclosure includes a reactor for catalytic dehydrogenation cracking of alkanes to olefins and a reaction disengager. The reaction disengager is located at an upper part of the reactor, and the reactor includes a dehydrogenation reaction section and a cracking reaction section, the dehydrogenation reaction section is located below the cracking reaction section, and an end of a catalyst regeneration sloped pipe is connected with the dehydrogenation reaction section.

An alkane catalytic dehydrogenation-cracking combined reaction process employs the above-mentioned reaction device for preparing alkenes by catalytic dehydrogenation-cracking of alkanes. Water vapor enters the dehydrogenation reaction section together with one or several light alkanes, which are in contact with a high-temperature regenerated catalyst to be subjected to a reaction. Then, a first oil gas 1 obtained after the dehydrogenation reaction and the catalyst enter the cracking reaction section together, and a second oil gas 2 obtained after the reaction in the cracking reaction section, and the catalyst enters the reaction disengager to separate the spent catalyst and the second oil gas 2.

A catalyst regeneration device of the present disclosure includes a regenerator accommodating a catalyst and a regeneration disengager, and a pipe wall of the regenerator is provided with fuel nozzles along the axial direction.

DETAILED DESCRIPTION

Figure 1:
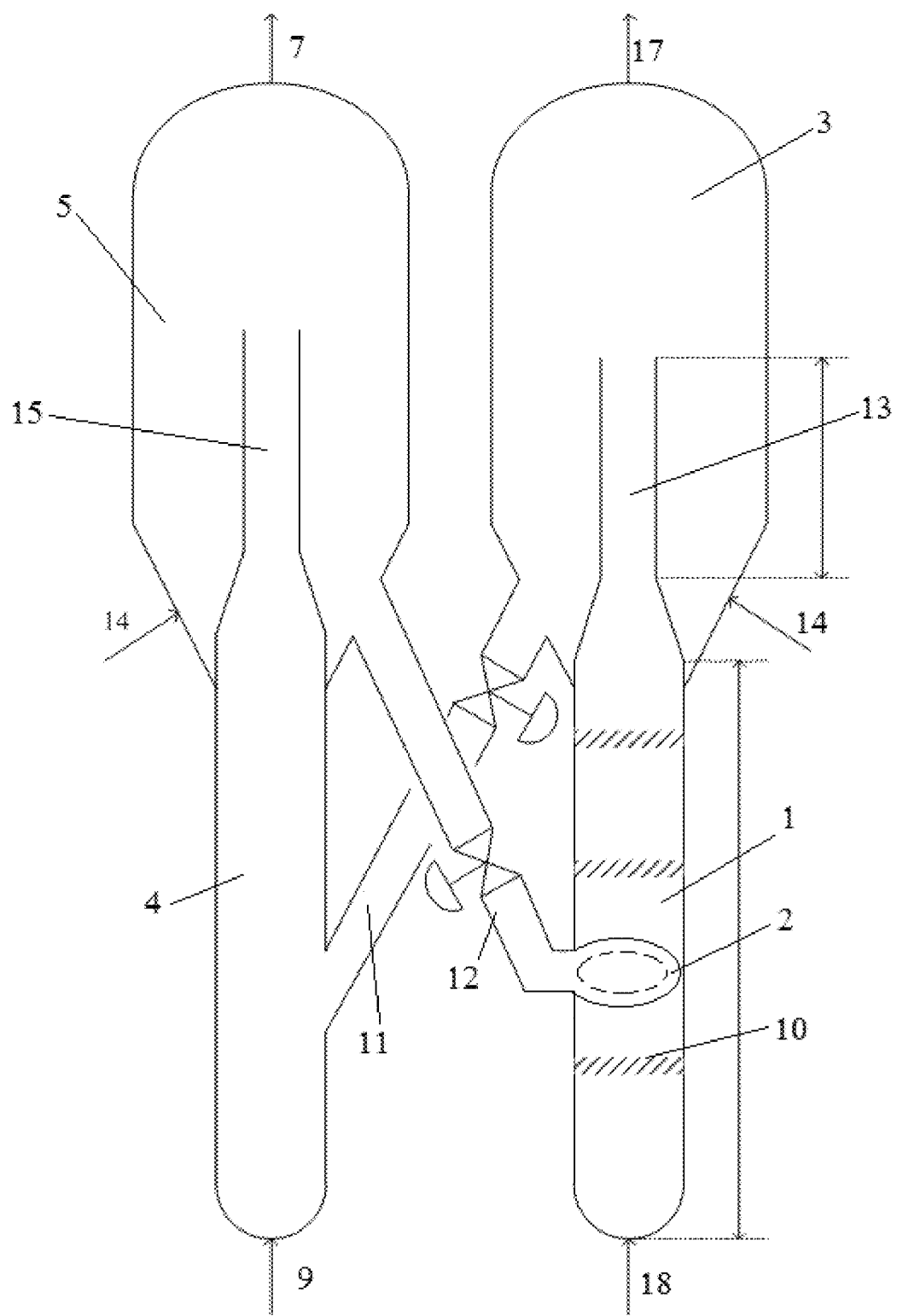
FIG. 1 shows an alkane dehydrogenation circulating fluidized bed reaction device of the present disclosure.

For a better understanding of the summary of the present disclosure, the technical solutions of the present disclosure will be clearly and fully described below in conjunction with the detailed description of the present disclosure, the embodiments and the accompanying drawings, and the following embodiments are intended to illustrate the present disclosure but are not intended to limit the scope of the present disclosure.

Experimental methods without specific conditions in the following embodiments are usually in accordance with conventional conditions or the conditions recommended by the manufacturer. Unless otherwise stated, all percentages, ratios, proportions, or parts are by weight.

Dense phase section: this section has a larger bed diameter, a lower gas velocity, and a higher catalyst fluidization density, which is conducive to gas-solid contact and reaction.

Dilute phase section: this section has a smaller bed diameter, a higher gas velocity, and a lower catalyst fluidization density. Objective: the linear velocity is increased so that the oil gas leave the reactor quickly, thereby reducing the secondary reaction of olefins; the low catalyst density is also advantageous in reducing secondary reactions, especially the formation of coke; requirements for catalyst delivery.

The term "mass space time" refers to a ratio of the mass of a catalyst to the mass of a feed per hour.

The term "superficial gas velocity" is a velocity at which the fluid escapes from the bed material after the bed is fluidized. It is an important operating parameter of a circulating fluidized bed.

The term "oil gas" refers to a sum of all reactants and products within the reaction device in the present disclosure.

The term "angle of repose", also referred to as an angle of repose, is a minimum angle between the inclined surface and a horizontal surface when an object placed on an inclined surface is in a critical state of sliding down along the inclined surface (i.e. as the angle of inclination increases, the object on the inclined surface will slide down more easily; the angle of this critical state is referred to as the angle of repose when the object reaches a state where it begins to slide down).

The "peripheral wall" of the reactor of the present disclosure refers to the wall of the reactor parallel to the central axis of the reactor.

In the present disclosure, the "upper ends" and the "lower ends" of all flow dividers arranged within the disengager are relative to the position of the outlet of the reactor, the "upper end" refers to the end relatively far away from the outlet of the reactor and the "lower end" refers to the end adjacent to the outlet of the reactor.

In the present disclosure, the cracking feedstocks generally include alkanes having a number of carbon atoms greater than or equal to 4, preferably n-butane, pentane, hexane, and the like. Dehydrogenation feedstocks typically include propane and ethane.

Unless otherwise defined, all technical and scientific terms used herein have the same meaning as those familiar to those skilled in the art. Furthermore, any methods and materials similar or equivalent to the content recorded can be used in the methods of the present disclosure. The preferred embodiments and materials described herein are exemplary only.

The circulating fluidized bed device for catalytic dehydrogenation of alkanes includes a reaction device and a regeneration device, and the reaction device, the regeneration device, the alkane catalytic cracking-dehydrogenation device and the reaction processes in these devices are described in further detail below.

In a first aspect, an alkane dehydrogenation circulating fluidized bed reaction device of the present disclosure includes a reactor and a reaction disengager, wherein the reaction disengager is located above the reactor, a reaction feedstock inlet is arranged on the reactor. The reactor is provided with a catalyst distributor through which a catalyst is sprayed into the reactor along a direction from the peripheral wall of the reactor to the center axis of the reactor. The reaction feedstock inlet is located below the catalyst distributor.

The catalyst distributor of the present disclosure can be of all feasible structures for realizing the above-mentioned method of spraying the catalyst.

In certain embodiments, the catalyst distributor is an annular pipe and an opening is formed on the annular pipe for allowing the catalyst to be sprayed.

Typically, the annular pipe is of a closed ring-like structure formed by a pipe with a circular cross section.

In certain embodiments, two or more openings are formed on the annular pipe, and the openings on the annular pipe are located at the side wall close to the central axis of the annular pipe and are evenly distributed.

In certain embodiments, a through opening is arranged on the side wall close to the central axis of the annular pipe and around the central axis.

A ring of through opening is arranged along the side wall, closest to the central axis, of the annular pipe, and the distance between the upper and lower edges of the opening may be equal and may also be unequal. For example, in the ring of opening, the distance between the upper and lower edges of one segment of the opening is relatively larger, while the distance between the upper and lower edges of another segment of the opening is relatively smaller. The "upper" and "lower" edges herein refer to the relative position of the opening when the central axis of the annular pipe is parallel to the central axis of the reactor.

In certain embodiments, based on a plane of the side wall of the annular pipe closest to the central axis, the opening for allowing the catalyst to be sprayed is arranged on the wall of the annular pipe on one side of the plane, and the direction of the opening faces the central axis of the annular pipe. The annular pipe is installed in the reactor, the opening is located above the above plane, so that the catalyst is sprayed obliquely upwards towards the central axis of the reactor.

In certain embodiments, when the annular pipe is provided with a plurality of openings, the openings are generally circular in shape.

In certain embodiments, at least two nozzles through which the catalyst is sprayed are arranged on the side, close to the central axis, of the annular pipe.

Wherein, a plurality of nozzles are evenly arranged on the side wall, close to the central axis, of the annular pipe, and the direction of the opening for allowing the catalyst to be sprayed is perpendicular to the central axis of the annular pipe, or the opening direction is inclined upwards. In this way, the catalyst can be sprayed perpendicularly towards the central axis through the nozzles, or sprayed into the reactor in an obliquely upward direction towards the central axis.

By the catalyst distributor of the present disclosure, a high-temperature regenerated catalyst is sprayed from the side of the reactor to the center through the catalyst distribution annular pipe, thereby effectively avoiding formation of a ring core structure of which the middle part is thin, and the side walls are thick near a feed section of the reactor when the catalyst enters the reactor. That is, near a catalyst inlet within the reactor, the catalyst concentration in the middle of the reactor is increased, which is advantageous to increase the contact efficiency between the oil gas and the catalyst near the catalyst inlet within the reactor, thus promoting alkane catalytic dehydrogenation reactions.

Additionally, through the catalyst distributor of the present disclosure, the high-temperature catalyst sprayed to the center of the reactor flows upward along the center of the reactor under the action of a lifting medium and then flows downward along the wall of the reactor. For the reaction temperature in the whole reactor, the temperature gradient in the axial direction decreases significantly, that is, the temperature change in the reactor is smaller. The side reactions of the alkane dehydrogenation reaction caused by local high temperature are reduced, and then the alkane catalytic dehydrogenation reaction is improved, that is, the conversion rate and selectivity of alkane dehydrogenation are improved.

The reactor of the present disclosure includes a dense phase section and a dilute phase section, wherein the dilute phase section is located above the dense phase section.

In certain embodiments, the catalyst distributor is located between 1/6 and 5/6, preferably between 1/2 and 2/3, of the height of the dense phase section of the reactor based on the bottom of the reactor.

Typically, the fluidization concentration of the catalyst below the catalyst inlet is higher and the fluidization concentration decreases during the ascending process. In the present disclosure, the catalyst distributor is located in the reactor at a distance of 1/6 to 5/6 of the height of the dense phase section from the bottom of the reactor, and in a process that the catalyst below the catalyst distributor rises along the axial direction, a high-temperature catalyst is continuously injected, so that the fluidization density does not decrease due to the catalyst introduction in the process of catalyst rising. Thus, in the dense phase section, the catalyst is in full contact with the oil gas, thereby promoting the catalytic dehydrogenation of alkanes. Otherwise, if the contact time is increased in order to allow the catalyst and oil gas to flow upward at the same time, the catalyst distributor is arranged at the bottom of the reactor, in the process of catalyst rising, the fluidization concentration decreased gradually, and the oil gas in the upper part of the dense phase section may have insufficient contact with the catalyst.

In the present disclosure, the dense phase section of the reaction is a tank of equal diameter. The dilute phase section is preferably a pipe of equal diameter or may be a pipe of unequal diameter.

The reaction device of the present disclosure does not only include the components defined in the present disclosure, and other components and structures of the reaction device can adopt the structures disclosed in the prior art.

The alkane dehydrogenation circulating fluidized bed reaction is combined with the regeneration device, the reaction device and the regeneration device are communicated with each other via a catalyst regeneration sloped pipe and a catalyst to-be-regenerated sloped pipe. The reaction device includes a reactor and a reaction disengager, the reaction disengager is located above the reactor, the reactor includes a dense phase section and a dilute phase section, and the dilute phase section extends into the reaction disengager;

The regeneration device includes a regenerator and a regeneration disengager section. The regeneration disengager section is located above the regenerator. The regenerator includes a regeneration dense phase section and a regeneration dilute phase section, and the regeneration dilute phase section extends into the regeneration disengager section.

The height of the catalyst within the annular gap between the delivery pipe in the dilute phase section and the wall of the reaction disengager can be controlled by increasing the height of a delivery pipe in the dilute phase section of the reactor. This height can be used to adjust the driving force of catalyst circulation on one hand, and can be used to adjust the effect of catalyst degassing and stripping on the other hand.

The greater the proportion of the height of the regeneration dilute phase section to the height of the regeneration disengager, the greater the catalytic driving force of regeneration within the regeneration disengager section and the better the effect of degassing and stripping. In this way, the amount of gas stripping nitrogen that is additionally introduced can be reduced when the regenerated catalyst enters the reactor, the better the effect of degassing and gas stripping, the lower the demand for gas stripping, that is, the cost is saved, and the more favorable the dehydrogenation reaction.

In a second aspect, the alkane dehydrogenation circulating fluidized bed reaction device of the present disclosure includes a reactor and a reaction disengager, wherein the reaction disengager is located above the reactor. An outlet of the reactor is located inside the disengager. And a primary cyclone separator, a primary cyclone riser, and a cover body are arranged within the disengager section. The cover body includes an upper part and a lower part, the upper part of the cover body is a truncated cone, and the lower part of the cover body is below the lower bottom surface of the truncated cone. The area of the opening at the lowermost end of the cover body is greater than the area of the outlet of the reactor. The outer periphery of the upper base of the truncated cone is connected with the outer periphery of the primary cyclone riser. Or the outer periphery of the upper base of the circular truncated cone is connected with the outer periphery of the primary cyclone above an inlet of the primary cyclone separator. And the part or the whole of the primary cyclone separator is located inside the cover body.

Preferably, the lower part of the cover body is a cylindrical structure.

The cylindrical structure of the lower part of the cover body can be equal or unequal in cross section perpendicular to the axial direction. That is, the lower part of the cover body can be a cylinder with a gradually reduced diameter from top to bottom, or a cylinder with a gradually expanded diameter from top to bottom. Preferably, the lower part of the cover body is a cylindrical structure.

The primary cyclone separator has any of the structures disclosed in the prior art and generally includes a primary cyclone separator body and a conveying part located under the body.

In one embodiment, an outlet of the conveying part of the primary cyclone separator is lower than the outlet of the reactor.

In one embodiment, the angle $\theta$ between the truncated cone generatrix and the lower bottom surface of the truncated cone-shaped part of the cover body is greater than the angle of repose of catalyst particles. In this way, it is ensured that the catalyst particles falling on the conical surface can freely slide off.

In certain embodiments, the area of the lowermost opening of the cover body is greater than or equal to the area of an outlet of a dilute phase delivery pipe. Preferably, the area of the lowermost opening of the cover body is 1.5-5 times, more preferably 2-3 times of the area of the outlet of the reactor.

Within the disengager section of the present disclosure, a cyclone separator is further arranged outside the cover body. Two or more cyclone separators may be arranged. Or two or more first-stage cyclone separators and two or more second-stage cyclone separators are arranged. The cyclone separators arranged outside the cover body are communicated with a gas collecting chamber within the disengager through a riser.

In certain embodiments, the outlet of the primary cyclone riser is not connected with the inlet of the first-stage cyclone separator. The outlet of the primary cyclone riser is higher than or equal to the inlet of the first-stage cyclone separator.

In certain embodiments, the outlet of the primary cyclone riser is connected with the inlet of the first-stage cyclone separator in a bell-and-spigot manner, and a gap is formed between the pipe walls of the inlet of the primary cyclone riser and the inlet of the first-stage cyclone separator for allowing the oil gas in the disengager to enter the cyclone separators.

In the present disclosure, the top end of the cover body in the disengager section is relatively far away from the outlet of the reactor. In certain instances, the top end of the cover body is about at a distance of a height of one cyclone separator from the outlet of the reactor. In addition, there is also a cylindrical part below the truncated cone. A part of the oil gas discharged from the outlet of the reactor flows into the disengager from the edge of the opening at the lower end of the cover body; another part of the oil gas discharged from the outlet of the reactor enters the cover body and directly enters the upper part of the disengager through the inlet of the primary cyclone separator. In this way, compared with the case where all the oil gas enter the disengager and flow upward, the oil gas in the present disclosure flows into the cyclone separator from the upper and lower directions of the disengager, so that the superficial gas velocity is much reduced, thereby reducing the amount of the catalyst carried by the upward flow of the oil gas and reducing the transport disengaging height (TDH).

In certain embodiments, within the disengager section, the lowermost end of the cover body is lower than the outlet of the reactor. That is, the plane where the lowermost end of the cover body is located is lower than the plane where the outlet of the reactor is located. It is convenient for the oil gas discharged from the outlet of the reactor to enter either the cover body or the disengager outside the cover body.

In certain embodiments, the disengager section includes a dense phase section and a dilute phase section, the lowermost end of the cover body is higher than the interface between the dilute phase section and the dense phase section, i.e. the lowermost end of the cover body is located within the dilute phase section of the disengager. Preferably, the lowermost end of the cover body is 0.5 m or above, more preferably 1 m or above higher than the interface between the dilute phase section and the dense phase section.

In certain embodiments, the inlet of the primary cyclone separator is not connected with the outlet of the reactor.

In certain embodiments, the outlet of the riser of the primary cyclone separator and the inlets of the first-stage cyclone separators are on the same horizontal plane, or the outlet of the riser of the primary cyclone separator is higher than the inlets of the first-stage cyclone separators.

The reactor of the present disclosure can include a dense phase section and a dilute phase section, both the dilute phase section and the dense phase section are of cylindrical structures of equal diameter, and the diameter of the dilute phase section is less than the diameter of the dense phase section. The reactor can also not be divided into the dense phase section and the dilute phase section, the reactor is a straight pipe, and the reactor is a tank of equal diameter.

In certain embodiments, the primary cyclone separator body is disposed coaxially with the reactor. The centerline of the primary cyclone separator body coincides with the centerline of the cover body.

Catalytic dehydrogenation of alkanes to olefins mainly refers to dehydrogenation of propane to propylene and dehydrogenation of butane to butene, and for the circulating fluidized bed, the problem of separation of oil gas, flue gas and the catalyst is highlighted.

The single-pass conversion rate of alkane dehydrogenation is limited by thermodynamic equilibrium, and the conversion rate is decreased exponentially with the increase of pressure. The reduction of the single-pass conversion rate means that under the condition that the processing capacity of fresh raw materials remains unchanged, the circulation capacity increases and the total feed capacity increases, resulting in an increase in investment and energy consumption. Therefore, the pressure of alkane dehydrogenation reaction should be as low as possible. After the pressure is designed to reduce to a certain extent, the only way to continue to reduce the pressure drop is the initial separation of the oil gas and catalyst.

If only inertial separation is relied upon, and a simple quick separation structure is arranged at the outlet of the dilute phase delivery pipe of the reactor, the pressure drop will be low, but the separation efficiency will not be high. Typically, a conventional umbrella cap shaped barrier is arranged at the upper part of the outlet of the reactor, the separation efficiency of the oil gas and catalyst can reach 75%, and when the barrier has an inverted L shape, the separation efficiency of the oil gas and catalyst can reach 85%. Therefore, the catalyst concentration in the oil gas entering the cyclone separator cannot be too low. The high concentration of the catalyst in the oil gas entering the cyclone separator will aggravate the attrition of the catalyst, thus increasing the catalyst consumption.

Furthermore, under the condition that the separation efficiency of the cyclone separator remains unchanged, the lower the catalyst content in the gas entering the cyclone separator, the lower the catalyst consumption. Therefore, the initial separation efficiency of the oil gas with the catalyst directly affects the catalyst consumption.

If other existing primary separation technologies with high separation efficiency are adopted, on one hand, the pressure drop will be large, at least a few kilopascals, and on the other hand, the catalyst attrition will be severe. In particular, alkane dehydrogenation is a strong endothermic reaction, and the heat of reaction and heat of temperature rise of part of the feedstocks are all supplied by the regenerant. The dehydrogenation reaction temperature is generally about 600° C. and the catalyst regeneration temperature is about 700° C., with a small temperature difference. Therefore, the catalyst/oil gas ratio of the reaction is high and the circulation rate of the catalyst is high. The circulation rate of the catalyst is high, so the attrition of the catalyst must be reduced as much as possible to reduce catalyst consumption. In addition to being closely related to the mechanical strength of the catalyst itself, the attrition is closely related to the gas velocity, the higher the gas velocity, the more severe the attrition. With a quick separation technique with a higher pressure drop such as primary cyclone, the separation efficiency of the catalyst can reach about 90%, but all the catalyst is subject to primary cyclone, which necessarily exacerbates the catalyst attrition.

In addition to the technical features disclosed in the present disclosure, the structures or components employed by other alkane catalytic dehydrogenation or alkane catalytic cracking reaction devices may employ the contents and structures disclosed in the prior art to ensure that the reactions described above proceed smoothly.

In a third aspect, the alkane dehydrogenation circulating fluidized bed reaction device of the present disclosure includes a reactor and a reaction disengager, wherein the reaction disengager is communicated with the reactor, an outlet of the reactor is located within a disengager section. A first flow divider and a second flow divider are arranged within the disengager section, and both the first flow divider and the second flow divider are located above the outlet of the reactor. The first flow divider is a component configured to reduce the gas velocity in the upward direction of the gas flow discharged from the outlet of the reactor. The second flow divider includes a second cover body of which both upper and lower ends are open, and a cross-sectional diameter of the lower opening is greater than that of the upper opening. The first flow divider is located in the second flow divider.

In the present disclosure, at least two layers of flow dividers are arranged in the reaction disengager, and most of the oil gas and catalyst discharged from the outlet of the reactor directly settle into a dense phase bed of the disengager section under the action of the first flow divider closest to the outlet of the reaction. The gas is divided into two parts, one part of the gas carries a part of the catalyst to flow upward along the gap between the first and second flow dividers. And another part of the gas flows upward obliquely from the outside of the second flow divider. The ratio of the two parts of the gas can be flexibly adjusted by adjusting the bottom area ratio and spacing of the first flow divider and the second flow divider, the distance between the first flow divider and the second flow divider, and the size of the top outlet of the second flow divider.

In certain embodiments, the first flow divider is a first cover body, the cross-sectional area of the first cover body gradually decreases from bottom to top, a lowermost end of the cover body is an opening, and it is a continuous surface from the lowermost end of the cover body to the top of the cover body.

Preferably, the first flow divider is of an inverted cone structure, or a spherical crown structure.

In certain embodiments, a cross-sectional area of the lowermost end (i.e., the end closest to the outlet of the reactor) of the first flow divider is greater than or equal to the cross-sectional area of the outlet of the reactor. Preferably, the cross-sectional area of the lowermost end of the first flow divider is greater than the cross-sectional area of the outlet of the reactor and less than 2 times of the cross-sectional area of the outlet of the reactor.

In one embodiment, the lowermost end of the first flow divider is lower than the outlet of the reactor. Preferably, the cross-sectional area of the annular gap formed between the outlet of the reactor and the first flow divider is less than or equal to the cross-sectional area of the outlet of the reactor.

In another embodiment, the lowermost end of the first flow divider is higher than the outlet of the reactor. Preferably, the cross-sectional area of the annular gap formed by the outlet of the reactor and the lower edge of the first flow divider is less than or equal to the cross-sectional area of the outlet of the reactor.

In certain embodiments, the first flow divider is preferably of an inverted cone structure, and the angle θ between the generatrix and the bottom surface of the cone is greater than the angle of repose of the catalyst particles. In this way, it is ensured that the catalyst particles falling on the conical surface can freely slide off.

In one embodiment, the first flow divider includes a first cover body having a conical structure of which the cross-sectional area gradually increases from bottom to top, two curves passing through the apex are on the cross section in a longitudinal direction of the first cover body passing through the apex of the cone, and the curvature of each curve first increases, and then decreases from the apex of the cone to the bottom edge of the cone.

In another embodiment, the first flow divider includes a first cover body having a conical structure of which the cross-sectional area gradually increases from bottom to top, and a conical surface of the conical structure gradually bends in a direction away from a centerline of the cone from the apex of the cone to the bottom edge of the cone.

Further, the first flow divider further includes a cavity having a conical structure of which the cross-sectional area gradually increases from top to bottom. The end, near the outlet of the reactor, of the cavity is a bottom surface; the end, away from the outlet of the reactor, of the first cover body is a bottom surface, and the bottom edge of the first cover body of the conical structure is connected with the bottom edge of the cavity.

Preferably, the cross-sectional area of the lowest end of the cavity with the conical structure of the first flow divider is greater than the cross-sectional area of the outlet of the reactor. More optionally, the cross-sectional area of the lowest end of the cavity with the conical structure of the first flow divider is greater than the cross-sectional area of the outlet of the reactor and less than 2 times of the cross-sectional area of the outlet of the reactor.

Figures 8A, 8B:
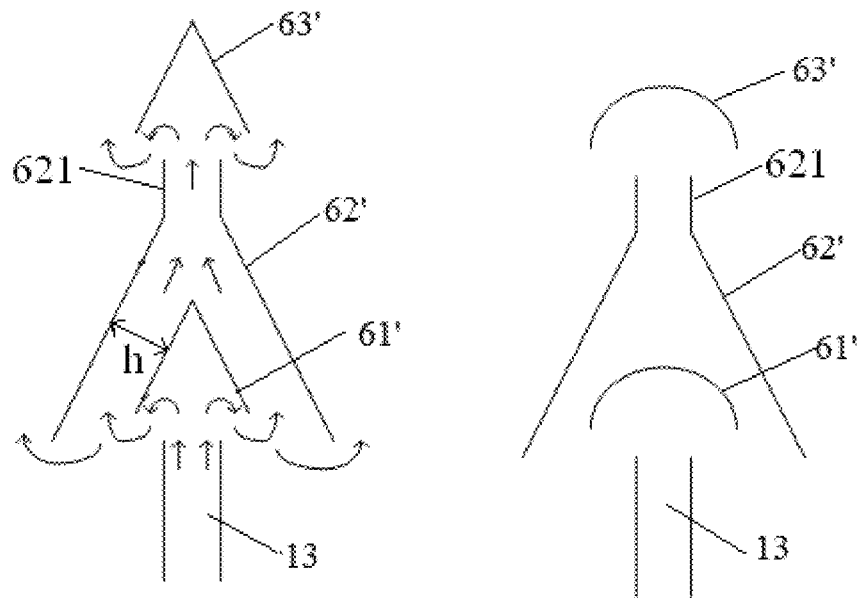
FIGS. 8A-8C are structural schematic diagrams of a quick separation assembly of the present disclosure.
Figure 8C:
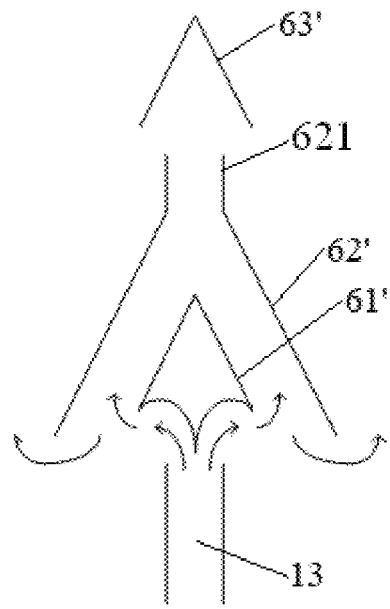

After the oil gas and the catalyst discharged from the outlet of the reactor are treated by the first flow divider as shown in FIG. 8C, most of the catalyst is blocked from entering the dense phase bed of the disengager. The gas is divided into two parts, one part of the gas carries a part of the catalyst to flow upward along the gap between the first and second flow dividers through the guide of the first flow divider, and another part of the gas flows upward obliquely from the outside of the second flow divider.

In certain embodiments, the second flow divider further includes a flow diversion pipe of equal diameter. An end of the flow diversion pipe is connected with the upper opening of the cover body. Preferably, the flow diversion pipe is a straight pipe of equal diameter or is a guide pipe of variable diameter.

In certain embodiments, the second flow divider is a truncated cone-shaped cover body, and the end of the truncated cone with the least cross section (the upper bottom surface) is connected with the flow diversion pipe.

The second flow divider is a truncated cone-shaped cover body and the angle between the generatrix and the lower bottom surface is greater than the angle of repose of the catalyst particles.

In certain embodiments, the second flow divider is of a spherical crown structure, and an outlet is formed on the spherical crown structure. Preferably, the outlet is formed on the uppermost end, i.e. away from the outlet of the reactor, of the spherical coronal structure.

The area of an outlet of the second flow divider is designed with an outlet gas velocity less than or equal to the gas velocity of the outlet of the dilute phase delivery pipe. That is, the cross-sectional area of the outlet of the second flow divider is greater than the cross-sectional area of the outlet of the reactor.

In certain embodiments, the cross-sectional area of the lowermost end of the second flow divider is greater than 1.5 times of the cross-sectional area of the lowermost end of the first flow divider.

In certain embodiments, the minimum spacing between the first flow divider and the second flow divider should be greater than the cross-sectional diameter of the outlet of the reactor.

By controlling or varying the spacing between the first flow divider and the second flow divider, the ratio (diversion ratio) of fluid entering the disengager directly and fluid continuing to flow upward through the gap between the first flow divider and the second flow divider can be adjusted. Preferably, the diversion ratio of the two fluids is preferably between $3/1$ and $1/1$.

Additionally, the position of the lowermost end of the second flow divider is higher than the interface of the dilute phase and the dense phase of the catalyst within the disengager section. More preferably, the position of the lowermost end of the second flow divider is at least 1 m higher than the interface of the dilute phase and the dense phase of the catalyst within the disengager.

In certain embodiments, a third flow divider is further arranged in the disengager section, the third flow divider is located above the second flow divider. The third flow divider is also a third cover body, and the third cover body has a cross-sectional area that gradually decreases from bottom to top. A lowermost end of the cover body is an opening, and it is a continuous face from the lowermost end of the cover body to the top of the cover body.

Preferably, the third flow divider is of an inverted cone structure, or a spherical crown structure.

Figure 11:
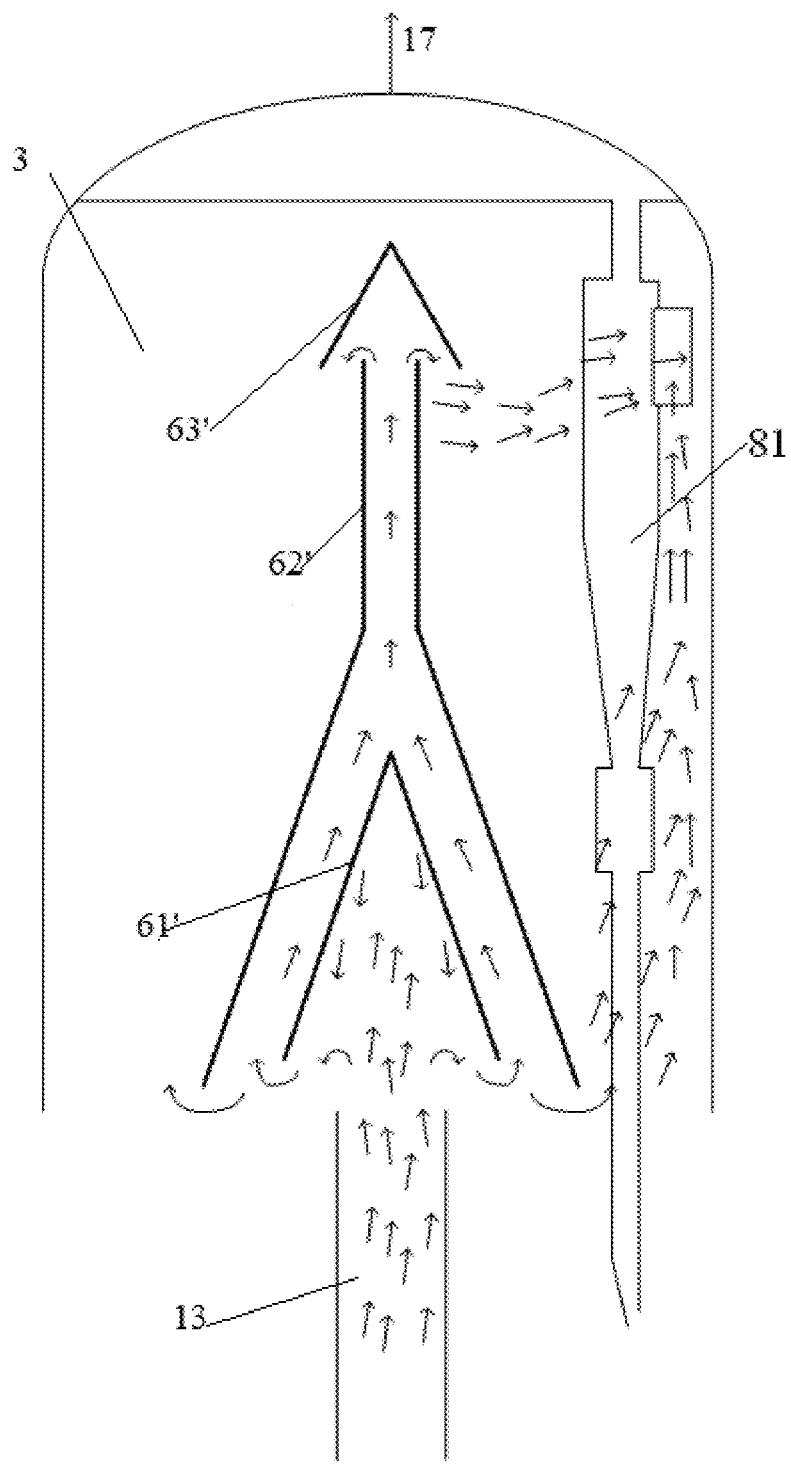
FIG. 11 is a schematic diagram of a gas flow within the disengager of FIG. 7.

Under the action of the third flow divider, one part of the catalyst entrained by gas flowing upward from the outlet of the second flow divider or the outlet of the flow diversion pipe settles down directly, and another part of the catalyst continues to be entrained by the gas. However the gas coming out from here generally flows horizontally or obliquely downward toward the inlet of the cyclone separator (as shown in FIG. 11), there is no upward force to balance the gravity of the catalyst, so this part of the catalyst will also settle naturally. It can be thus seen that the combined arrangement of the multi-layer flow dividers further reduces catalyst entrainment and promotes catalyst disengager by altering the flow field distribution.

In certain embodiments, a cross-sectional area of the lowermost end of the third flow divider is greater than or equal to a cross-sectional area of the outlet of the second flow divider. Or the cross-sectional area of the lowermost end of the third flow divider is greater than or equal to the cross-sectional area of the outlet of the flow diversion pipe of the second flow divider.

In certain embodiments, the lowermost end of the third flow divider is lower than the position of the outlet of the flow diversion pipe of the second flow divider. Preferably, the cross-sectional area of the annular gap formed between the outlet of the flow diversion pipe and the third flow divider is greater than or equal to the cross-sectional area of the outlet of the flow diversion pipe. Preferably, the cross-sectional area of the annular gap formed between the outlet of the flow diversion pipe and the third flow divider is greater than the cross-sectional area of the outlet of the reactor.

In another embodiment, the lowermost end of the third flow divider is higher than the position of the outlet of the flow diversion pipe of the second flow divider. Preferably, the cross-sectional area of the annular gap formed between the outlet of the flow diversion pipe and the lower edge of the third flow divider is greater than or equal to the cross-sectional area of the outlet of the flow diversion pipe. Preferably, the cross-sectional area of the annular gap formed between the outlet of the flow diversion pipe and the lower edge of the third flow divider is greater than the cross-sectional area of the outlet of the reactor.

In certain embodiments, the third flow divider is preferably of an inverted cone structure, and the angle θ between the generatrix and the bottom surface of the cone is greater than the angle of repose of the catalyst particles. In this way, it is ensured that the catalyst particles falling on the conical surface can freely slide off.

Each of the first, second and third flow dividers of the present disclosure is mounted in the reaction disengager by means of connections commonly used in the art.

Within the reaction disengager of the present disclosure, cyclone separators are also arranged outside the first, second and third flow dividers. Two or more cyclone separators may be provided. Or two or more first-stage cyclone separators are provided, and two or more second-stage cyclone separators are provided. The cyclone separator disposed outside the cover body is communicated with a gas collecting chamber within the disengager through a riser.

In certain embodiments, the outlet of the second flow divider or the outlet of the flow diversion pipe is higher than or equal to the height of the inlet of the cyclone separator.

In certain embodiments, the inlets of two or more cyclone separators in the disengager section are arranged close to the wall of the disengager section. Preferably, the inlets of the cyclone separators are arranged in a circumferential direction. For example, the inlets of the cyclone separators are arranged in a clockwise direction or in a counter-clockwise direction.

In this manner of arranging the cyclone separators of the present disclosure, the gas within the entire disengager is rotated along the same direction, facilitating that the catalyst suspended within the disengager section is "thrown" towards the wall of the disengager section under the action of centrifugal force and slides down along the wall into the dense phase bed. Further, the amount of catalyst entering the cyclone separators will be reduced.

The oil gas in the present disclosure flows into the cyclone separators from the upper and lower directions of the disengager, so that the superficial gas velocity is much reduced, thereby reducing the amount of the catalyst carried by the upward flow of the oil gas and reducing the transport disengaging height (TDH).

Catalytic dehydrogenation of alkanes to olefins mainly refers to dehydrogenation of propane to propylene and dehydrogenation of butane to butene, and for the circulating fluidized bed, the problem of separation of oil gas, flue gas and the catalyst is highlighted.

The dehydrogenation of alkanes to alkenes is a reversible reaction limited by thermodynamic equilibrium, and the equilibrium conversion rate increases with the decrease of pressure. In order to ensure safety of operation of the device, the pressure of the reaction is determined based on the pressure drop of the outlet of the reaction catalyst bed to the inlet of the rich gas compressor under the condition of ensuring that the inlet pressure of a rich gas compressor is slightly positive. Under a certain inlet pressure of the rich gas compressor, the lower the pressure drop from the outlet of the reaction catalyst bed to the inlet of the rich gas compressor, the lower the pressure of the reaction and the more favourable to the dehydrogenation reaction. Therefore, design optimization must be done for each link, such as quick separation of oil gas and the catalyst at the outlet of the reactor, cyclone separators, pipelines, heat exchange and cooling of oil gas, and water washing, to reduce the pressure drop in each link by every means.

In addition, alkane dehydrogenation is a strong endothermic reaction, heating of oil gas, and the amount of heat required to be absorbed for the reaction are entirely provided by means of the high-temperature regenerant, so that the amount of catalyst circulation is large. The amount of catalyst circulation is large and attrition is exacerbated and the resulting catalyst consumption must increase. For the size of attrition, the gas velocity is a decisive factor. Avoiding the high-speed movement of a large amount of catalysts as much as possible is a necessary option to reduce catalyst attrition. In a circulating fluidized bed dehydrogenation reactor regeneration system, the cyclone separator has a highest gas velocity, with an inlet linear velocity substantially about 20 m/s.

According to our laboratory observations, for most catalysts, such as the dehydrogenation catalyst disclosed in ZL201110123675.1 developed by the inventors, attrition phenomena occur when the gas velocity exceeds 10 m/s. And catalyst severe attrition phenomena occur when the gas velocity reaches 14 m/s. Therefore, in the design of the dehydrogenation reaction regeneration system, in addition to the cyclone separator, the gas velocity exceeding 10 m/s is avoided as much as possible, and is preferably controlled to be 7 m/s or below. For the cyclone separator, the concentration of the catalyst entering the cyclone separator is to be reduced as much as possible. Quick separation of the oil gas and the catalyst is very important to reduce the concentration of the catalyst at the inlet of the cyclone separator. The disengager provided in the disclosure can effectively reduce the concentration of the catalyst at the inlet of the cyclone separator and well separate the catalyst from the oil gas, whether in the catalytic dehydrogenation reaction, catalytic cracking reaction or catalyst regeneration reactor.

In a fourth aspect, a regeneration device for an alkane dehydrogenation catalyst includes a regenerator containing a catalyst and a regeneration disengager located above the regenerator. The regenerator includes a dense phase section and a dilute phase section, and the pipe wall of the dense phase section is provided with fuel nozzles along the axial direction. The dilute phase section of the regenerator is located above the dense phase section.

In one embodiment, the pipe wall of the dense phase section of the regenerator is provided with a plurality of fuel nozzles along the axial direction. Preferably, 3-10 fuel nozzles, preferably 4-6 fuel nozzles are arranged on the pipe wall of the dense phase section of the regenerator along the axial direction.

Wherein, the spacing between the fuel nozzles may or may not be equidistant, preferably the fuel nozzles are equidistant.

In certain embodiments, the bottom of the dense phase section of the regenerator is provided with a fuel and air inlet.

In the regeneration device of the present disclosure, air enters the regenerator from the bottom of the regenerator and fuel is injected from different height positions in the axial direction of the dense phase section of the regenerator. In the regenerator, during the upward movement of the fuel and the spent catalyst from the lower part of the regenerator, the more complete the combustion, the higher the temperature. The fuel is introduced at different height positions in the axial direction, which effectively avoids the problem of local high temperatures caused by injection of the fuel from the bottom. That is, the temperature difference within the dense phase section of the regenerator is small. If the local temperature inside the regenerator is too high, on one hand, it will cause destruction of the catalyst, and on the other hand, it will lead to the generation of NOx. In addition, the fuel is injected from different height positions in the axial direction, and the fuel injected afterwards also has a reducing effect on the NOx produced previously. In this way, the concentration of NOx in the flue gas is reduced both in terms of NOx generation and reduction by means of the injection of the fuel.

In certain embodiments, the highest fuel nozzle is arranged at a distance of ½ to ⅔ of the total height of the dense phase section of the regenerator from the bottom of the regenerator, based on the bottom of the regenerator. That is, the fuel nozzles are arranged on the wall, between the bottom of the regenerator and ½-⅔ of the height of the dense phase section, of the regenerator.

In certain embodiments, the highest fuel nozzle is at a distance of 2-3 m from the top of the dense phase section of the regenerator.

The fuel nozzles arranged in the pipe wall of the regenerator should avoid a spent catalyst inlet, that is to say, the fuel nozzles are not on the same horizontal plane as the spent catalyst inlet.

In order to ensure that the fuel at the bottom of the regenerator can ignite smoothly, the spent catalyst enters the regenerator as close as possible to the bottom of the regenerator. In addition, an external circulation pipe of the regenerator can be arranged to lead a part of the high-temperature regenerant settled from the disengager section of the regenerator back to the lower part of the regenerator to avoid flameout in the regenerator, especially when using gaseous fuels, such as natural gas, dry gas and other fuels with high spontaneous combustion point.

In certain embodiments, a grating or mesh made of a ferrous material, preferably, a stainless steel mesh is arranged in the regeneration disengager. The stainless steel material or ferrous material herein can be resistant to the temperature of the catalyst regenerator.

1-5 layers of gratings or meshes, preferably 2-3 layers of gratings or meshes are arranged in the regeneration disengager.

Within the regeneration disengager, gases derived from the regenerator include CHx, CO and NOx. In the disengager environment, such as temperature, under the catalysis of ferrous materials or stainless steel, reducing gases such as CHX and Co are reduced, and NOx generates nitrogen. In this way, the concentration of NOx in flue gas is further reduced.

In another aspect, a regeneration method for an alkane dehydrogenation catalyst is provided. A spent catalyst enters a regenerator, air and a part of fuel enters the regenerator from a lower part of the regenerator, other fuel enters the regenerator from fuel nozzles arranged at the pipe wall of the regenerator, and flue gas produced after a combustion reaction is discharged through a flue gas outlet at a top of the regeneration disengager.

The regeneration method of the present disclosure is carried out in the above-mentioned regeneration device. And 3-10 fuel nozzles, preferably 4-6 fuel nozzles are arranged on the pipe wall of the dense phase section of the regenerator along the axial direction.

In certain embodiments, the amount of fuel injected through each fuel nozzle is the same.

In certain embodiments, the amount of fuel injected through each fuel nozzle gradually decreases from bottom to top along the axial direction.

Through the regeneration method of the present disclosure, the concentration of NOx in the flue gas can be reduced well. The amount of fuel required in treating an equivalent amount of the spent catalyst is also reduced. That is, the cost of catalyst regeneration is reduced and pollutant gas emissions are reduced.

In certain embodiments, the superficial gas velocity at the top of the dense phase bed of the regenerator is advantageously in the range from 0.01 m/s to 1 m/s, preferably in the range from 0.05 m/s to 0.5 m/s.

The temperature in the regenerator of the present disclosure is between 600° C. and 850° C., preferably between 630° C. and 750° C. The temperature in the regeneration disengager is also within this range.

The fuel may be a gaseous fuel or a liquid fuel free of sulfur and metal.

In the present disclosure, the dense phase section of the regenerator is a tank of equal diameter and the dilute phase section is preferably a pipe of equal diameter. And the diameter of the dilute phase section is smaller than the diameter of the dense phase section. The dense phase section and the dilute phase section of the regenerator may also be in unequal diameter.

The regeneration device of the present disclosure does not include only the components defined in the present disclosure, and other components as well as the structure of the regeneration device can adopt the structures disclosed in the prior art.

The catalyst regeneration device of the present disclosure can be used in conjunction with any of the alkane dehydrogenation catalyst devices described above.

The catalyst regeneration device of the present disclosure has at least the following advantages:

1) In a simple way of injecting fuel at different axial positions of the regenerator, the problem of excessive local temperature in the regenerator is effectively avoided and the NOx generation is effectively reduced.
2) By additionally arranging a stainless steel mesh or grating within the disengager section of the regenerator, NOx is reduced to nitrogen by using a small amount of reducing gas in the flue gas under the catalytic action of stainless steel, thereby solving the problem of emission of NOx in flue gas.

The following is further described with reference to specific drawings and specific examples:

EMBODIMENT 1

Figure 2:
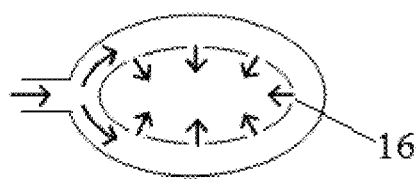
FIG. 2 is a structural schematic diagram of one embodiment of a catalyst distributor of the present disclosure.

As shown in FIGS. 1 and 2, the reaction device for catalytic dehydrogenation of alkanes provided in the present disclosure is used in conjunction with the catalyst regeneration device provided in the present disclosure. The two sets of the devices can be used separately, and are respectively in conjunction with other reaction devices or catalyst regeneration devices of the prior art.

According to the circulating fluidized bed alkane catalytic dehydrogenation reaction-regeneration device of this embodiment, the reaction device and the regeneration device are arranged in parallel.

The reaction device for the catalytic dehydrogenation of alkanes includes a reactor and a reaction disengager 3, and both the reactor and the reaction disengager are tanks. The reaction disengager 3 is located above the reactor. The reactor includes a dense phase section 1 and a dilute phase section 13. And the reactor is provided with a catalyst distributor 2. Both the dense phase section 1 and the dilute phase section 13 are of equal diameter structures and the dilute phase section 13 extends into the reaction disengager 3. The catalyst distributor 2 is located between ⅙ and ⅚, preferably ½ and ⅔ of the height of the dense phase section 1 of the reactor, based on the bottom of the reactor. And the catalyst distributor 2 is arranged above an alkane dehydrogenation feedstock inlet.

A few layers of gratings 10 are arranged within the dense phase section 1 of the reactor.

Referring to FIG. 2, the catalyst distributor 2 is an annular pipe, the side wall close to the central axis of the annular pipe is evenly provided with a plurality of openings along the circumferential direction. Or, the opening for allowing the catalyst to be sprayed is formed on the wall of the annular pipe on one side of the plane based on a plane where the side wall, closest to the central axis, of the annular pipe is located, and the opening direction is toward the central axis of the annular pipe, with reference to the reaction device of FIG. 1, that is, in this case, the opening for allowing the catalyst to be sprayed is located above the plane, so that the catalyst is sprayed obliquely upward towards the center axis of the reactor.

Figure 3:
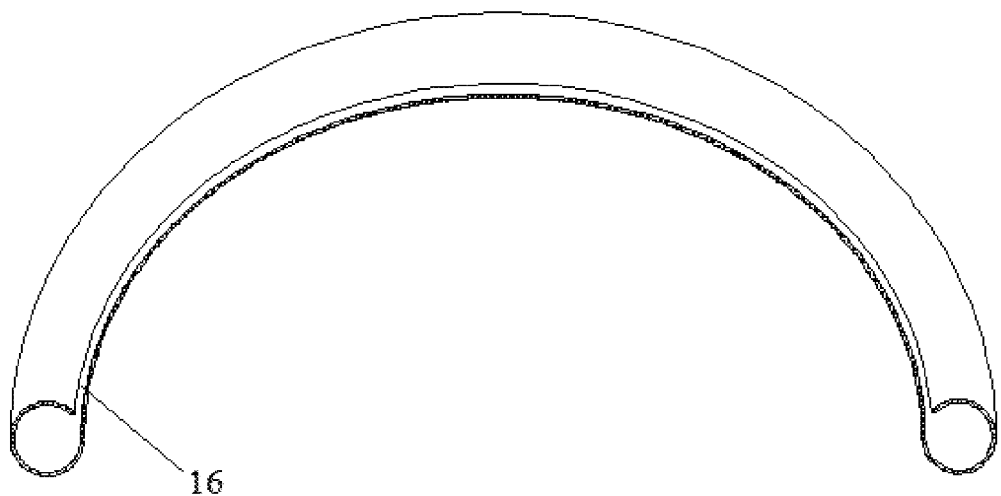
FIG. 3 is a cross-sectional view of another embodiment of the catalyst distributor of the present disclosure.

Referring to FIG. 3, the catalyst distributor 2 is an annular pipe, a through opening 16 is formed on the side wall close to the central axis of the annular pipe and around the central axis. The spacing of the upper and lower edges of the opening is equal.

The regeneration device includes a regenerator and a regeneration disengager 5, both the regenerator and a regenerator disengager section are tanks. The regenerator includes a regeneration dense phase section 4 and a regeneration dilute phase section 15, both the regeneration dense phase section 4 and the regeneration dilute phase section 15 are of equal diameter structures, and the regeneration dilute phase section 15 extends into the regeneration disengager 5.

One end of the catalyst regeneration sloped pipe 12 is connected with the regeneration disengager, the other end of the catalyst regeneration sloped pipe 12 is connected with the dense phase section 1 of the reactor. One end of the catalyst to-be-regenerated sloped pipe 11 is connected with the reaction disengager 3 and the other end of the catalyst to-be-regenerated sloped pipe 11 is connected with the regeneration dense phase section 4. In the dense phase section 1 of the reactor, the catalyst regeneration sloped pipe 12 enters the reactor through the reactor wall and is connected with the catalyst distributor 2, or the catalyst regeneration sloped pipe 12 is integrated with the catalyst distributor 2. In the regeneration disengager 5 of the regeneration device, due to the higher height of the dilute phase section of the regenerator, the higher the height of the catalyst within the annular gap between the dilute phase section and the wall of the regeneration disengager, the greater the driving force is given to the regenerated catalyst in the regeneration disengager, which is beneficial for the regenerated catalyst to enter the catalyst distributor 2 through the catalyst regeneration sloped pipe. As a result of this greater driving force given to the regenerated catalyst, the amount of a lifting medium, such as nitrogen, introduced into the reactor is reduced, and thus the catalyst degassing effect in the regeneration disengager is also greatly improved.

The specific process flow includes: alkane catalytic dehydrogenation feedstocks 18 enter the reactor from the lower part of the dense phase section 1 of the reactor, the oil gas and the catalyst flow upwards side by side within the reactor, and the feedstocks are subjected to a reaction within the dense phase section 1 of the reactor. The reaction product enters the reaction disengager 3 through the dilute phase section 13, rapid gas-solid separation is performed by means of the cyclone separator, the oil gas 17 leaves the reaction disengager and enters the subsequent separation system. The settled spent catalyst is stripped by a stripping medium 14, such as water vapor, and then enters the dense phase section 4 of the regenerator through the to-be-regenerated sloped pipe 11. The bottom of the dense phase section 4 of the regenerator is injected with air and the fuel 9 for combustion, and the coke on the surface of the spent catalyst is burned at the same time. The regenerated flue gas and the catalyst flow upwards side by side in the regenerator and enter the regeneration disengager 5 through the dilute phase section 15 to be subjected to gas-solid separation, and the flue gas 7 leaves the regeneration disengager and is discharged after energy recovery, washing and dust removal. The settled regenerated catalyst is stripped by a stripping medium 14, such as nitrogen, passes through the regeneration sloped pipe 12, and enters the dense phase section 1 of the reactor from the side of the reactor through the catalyst distributor 2.

Figure 4:
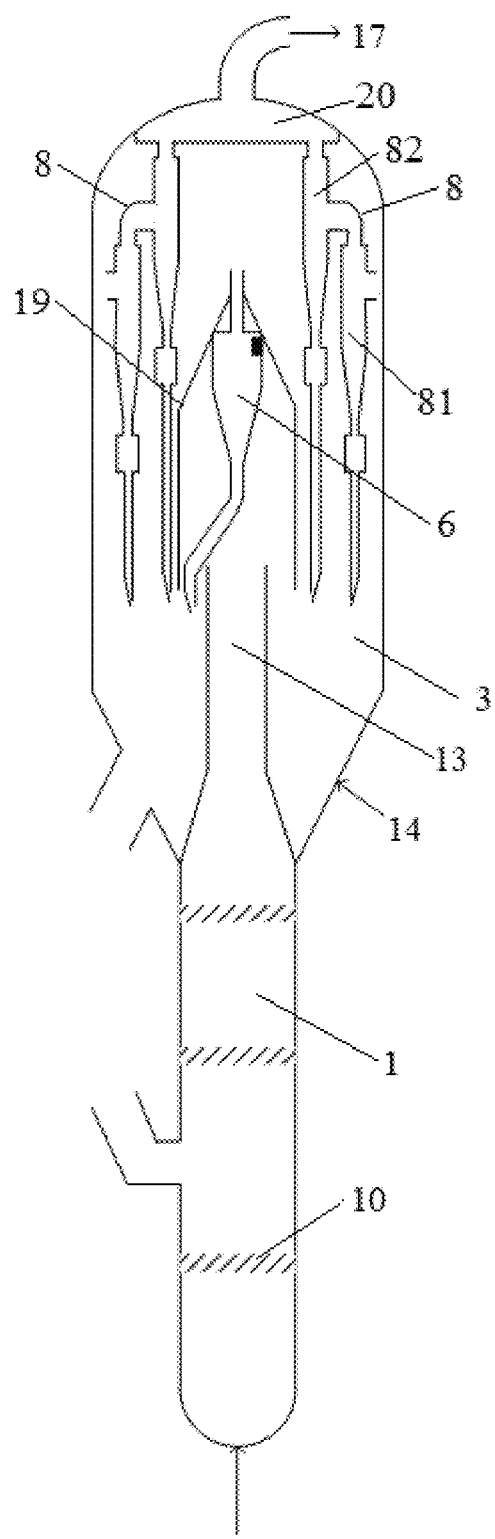
FIG. 4 is a structural schematic diagram of a reaction disengager of the reaction device of the present disclosure.

The reaction disengager of the reaction device in this embodiment may adopt any of the structures disclosed in the prior art and may also adopt the structure shown in FIG. 4.

EMBODIMENT 2

Referring to FIG. 4, an alkane catalytic dehydrogenation reaction device includes a reactor and a reaction disengager 3, wherein the reactor includes a dense phase section 1 and a dilute phase section 13, and the dilute phase section 13 extends into the reaction disengager 3.

Figure 5:
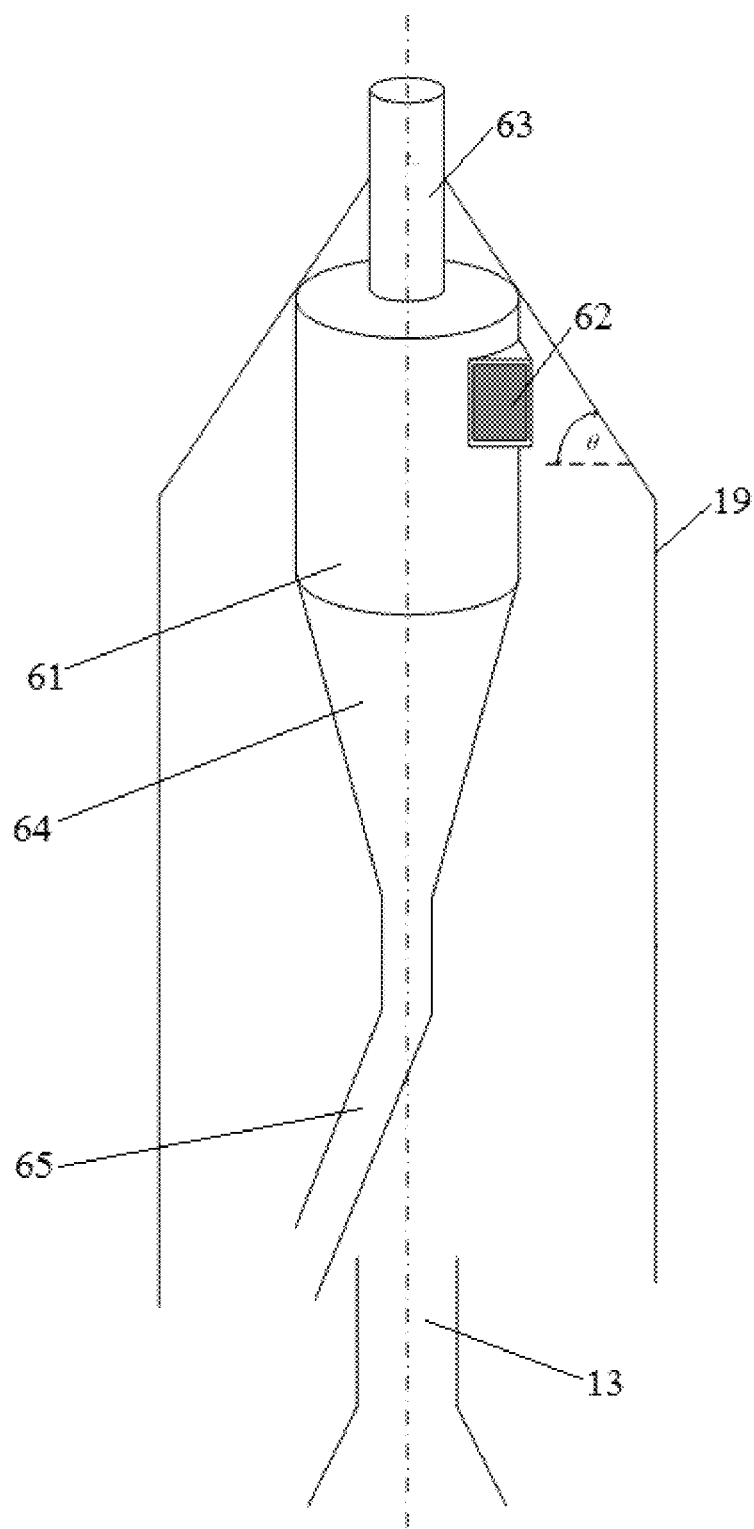
FIG. 5 is a structural schematic diagram of a cover body and a primary cyclone separator within a disengager section of FIG. 4.

An umbrella cap cyclone quick separation assembly is arranged in the reaction disengager 3, the umbrella cap cyclone quick separation assembly includes a primary cyclone separator 6 and a cover body 19. As shown in FIG. 5, the primary cyclone separator 6 includes, in sequence from top to bottom, a cylindrical body 61, an inverted cone 64 and a conveying part 65. An inlet 62 of the primary cyclone separator 6 is arranged on the upper part of the cylindrical body 61, and the gas flow enters the primary cyclone separator 6 in a tangential direction from the inlet 62. A riser 63 is arranged at the top of the primary cyclone separator 6, and is communicated with the cylindrical body 61 of the primary cyclone separator 6, and the oil gas or flue gas entering the primary cyclone separator 6 is discharged through the riser 63. The cover body 19 includes two parts, the upper part is of the shape of a truncated cone, the lower part is a cylinder, and the cover body may be integrally formed. The edge of the upper end (i.e. the upper bottom surface of the circular truncated cone) of the cover body 19 is connected with the outer periphery of the riser 63, and the primary cyclone separator 6 is placed in the cover body. And the lower end face of the cover body 19 is lower than the outlet of the dilute phase section 13 and the lower end face of the cover body 19 is located within the dilute phase section of the disengager.

The angle between the generatrix and the lower bottom surface of the truncated cone-shaped upper part of the cover body 19 is greater than the angle of repose of the catalyst particles. That is, the size of the angle of the circular truncated cone is related to the angle of repose of the catalyst particles used, so that a downward flow of the catalyst can be guaranteed.

The cross-sectional area of the lower opening of the cover body 19 is greater than the cross-sectional area of the outlet of the dilute phase transport section 13.

In this embodiment, the centerlines of the cylindrical body 61, the inverted cone 64, the cover body 19 of the primary cyclone separator 6 and the centreline of the reactor coincide. The outlet of the conveying part 65 should be far away from the outlet of the dilute phase section 13, and otherwise the catalyst of the primary cyclone separator 6 is not conducive to being discharged from the conveying part due to the influence of the upward gas flow of the dilute phase section 13.

In this embodiment, the inlet 62 of the primary cyclone separator 6 is not connected with the outlet of the dilute phase section 13.

Within the reaction disengager 3, the space outside the cover body 19 is also provided with a cyclone separator 8, and a gas collecting chamber 20. In this embodiment, two sets of cyclone separators are provided, and each set of the cyclone separator includes a first-stage cyclone separator 81, and a second-stage cyclone separator 82 communicated with the gas collecting chamber 20 via a riser. The inlet of the first-stage cyclone separator 81 and the inlet 62 of the primary cyclone separator 6 are in the same horizontal plane, or the inlet of the first-stage cyclone separator 81 is slightly lower than the inlet 62 of the primary cyclone separator 6.

Figure 6:
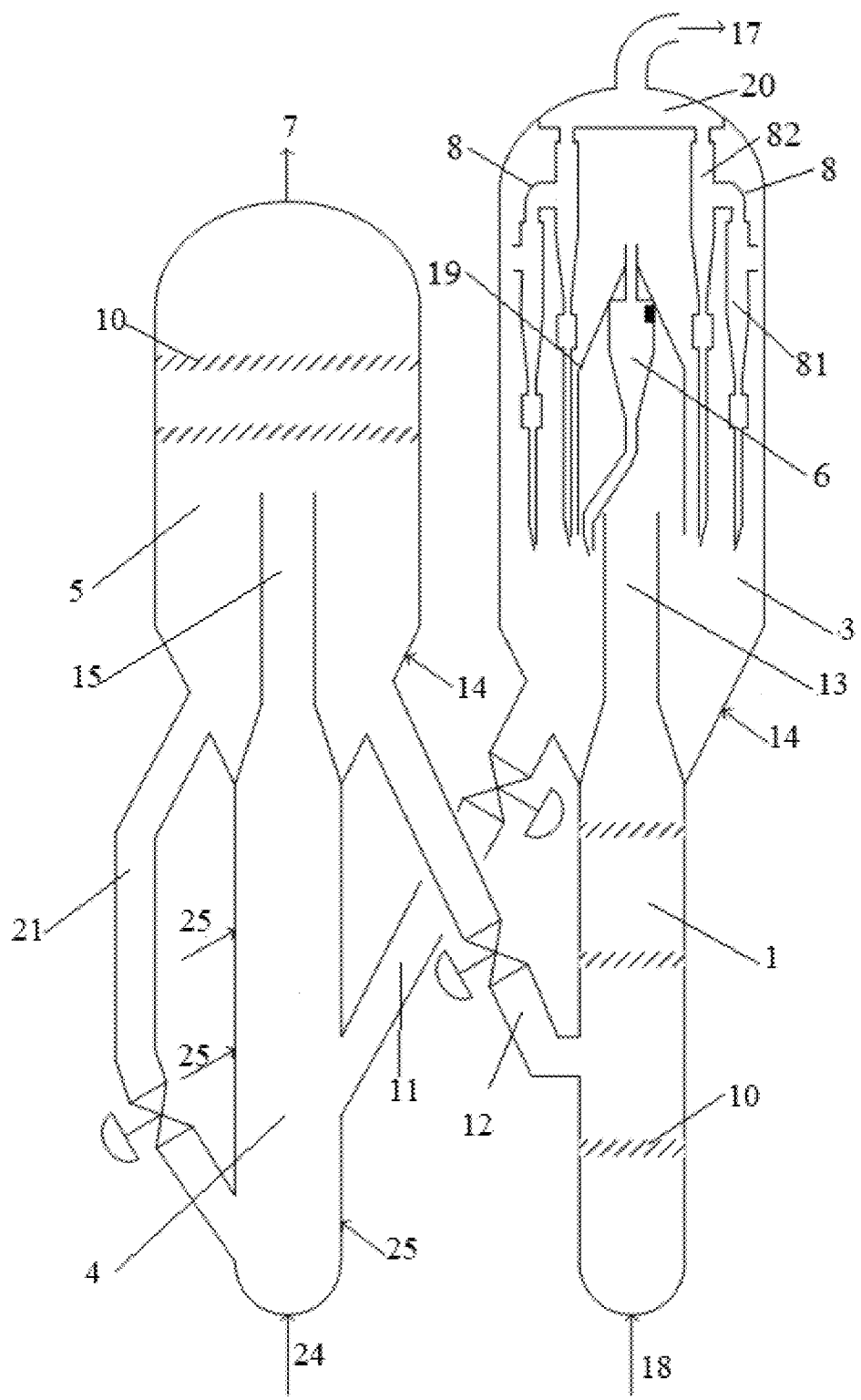
FIG. 6 is one structural schematic diagram of a circulating fluidized bed reaction-regeneration device of the present disclosure.

Referring to FIG. 6, the reaction device described above is connected with the regeneration device to realize an alkane dehydrogenation circulating reaction. The regeneration device of this embodiment includes a regenerator and a regeneration disengager section 5, and both the regenerator and the regeneration disengager section are tanks. The regenerator includes a regeneration dense phase section 4 and a regeneration dilute phase section 15, both the regeneration dense phase section and the regeneration dilute phase section are of equal diameter structures, and the regeneration dilute phase section 15 extends into the regeneration disengager section 5. The outside of the regenerator is provided with an external circulation pipe 21, one end of the external circulation pipe 21 is connected with the regenerator disengager section 5 and the other end of the external circulation pipe 21 is connected with the lower part of the regenerator for circulating the high temperature catalyst to the lower part of the regenerator. Two layers of gratings 10 are arranged within the regenerator disengager section 5. One end of the regeneration sloped pipe 12 is connected with the lower side of the regenerator disengager section 5 and the other end of the regeneration sloped pipe 12 is communicated with the dense phase section 1 of the reactor to facilitate transport of the regenerated catalyst from the regeneration device into the reactor. One end of the to-be-regenerated sloped pipe 11 is connected with the lower side of the reaction disengager 3 and the other end of the to-be-regenerated sloped pipe 11 is connected with the regenerator to facilitate transport of the spent catalyst from the reaction device into the regeneration reaction device.

A specific alkane dehydrogenation circulating fluidized bed process flow includes: the alkane catalytic dehydrogenation feedstocks 18 enter the reactor from the lower part of the dense phase section of the reactor, the oil gas is in sufficient contact with the catalyst for catalytic dehydrogenation in the dense phase section 1 of the reactor. The oil gas and the catalyst after catalytic dehydrogenation then enter the reaction disengager 3 through the dilute phase transport pipe 13. A part of the oil gas enters the cover body 19 and another part of the oil gas enters the disengager outside the cover body for rapid gas-solid separation by the primary cyclone separator 6 and the cyclone separator 8. Oil gas 17 enters the gas collecting chamber 20 and is discharged from the reaction device through the outlet of the disengager, leaves the reactor and enters a subsequent separation system. The settled spent catalyst is stripped by a stripping medium 14, such as water vapor, and then enters the dense phase section 4 of the regenerator through the to-be-regenerated sloped pipe 11. The bottom of the dense phase section 4 of the regenerator is injected with air 24 and fuel 25, the air 24 and the fuel 25 enter the dense phase section of the regenerator through two inlets at the bottom of the regenerator and at the side wall of the dense phase section 4, and the coke on the spent catalyst is burned at the same time. The regenerated flue gas and the catalyst flow upwards side by side and enter the regenerator disengager section 5 through the dilute phase section to be subjected to gas-solid separation, and the flue gas 7 leaves the regenerator and is discharged after energy recovery, washing and dust removal. The settled regenerated catalyst is stripped by a stripping medium 14, such as nitrogen, passes through the regeneration sloped pipe 12, and enters the dense phase section 1 of the reactor from the side of the reactor through the catalyst distributor. The reaction is repeated in this way.

EMBODIMENT 3

This embodiment is exemplified by an alkane catalytic dehydrogenation reaction device, and the reaction device of the present disclosure is further described in detail in combination with FIGS. 7-8, and 10-11.

Figure 7:
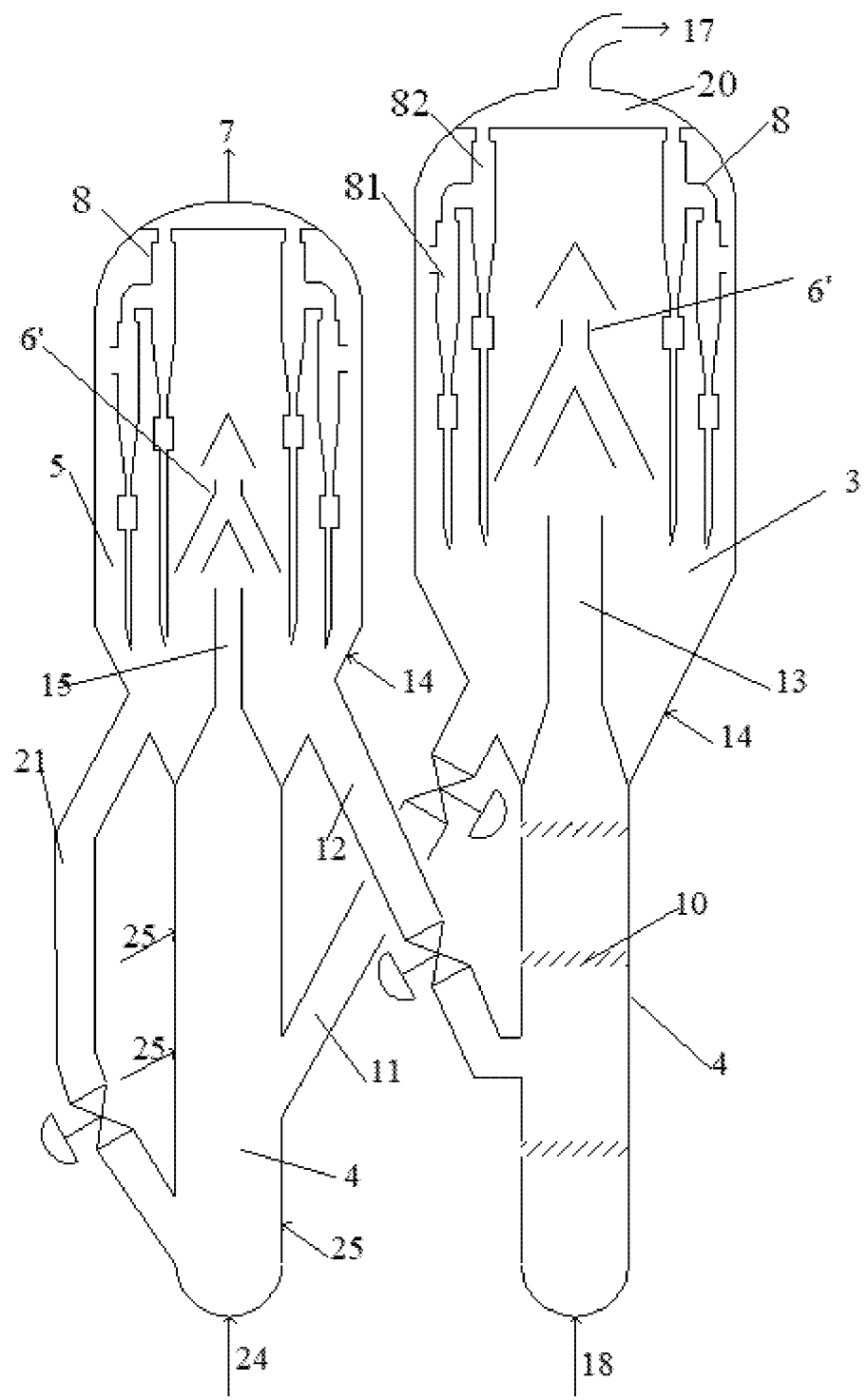
FIG. 7 is another structural schematic diagram of the circulating fluidized bed reaction-regeneration device of the present disclosure.

As shown in FIG. 7, the alkane catalytic dehydrogenation reaction device includes a reactor and a reaction disengager 3. The reactor includes a dense phase section 1 and a dilute phase section 13, wherein the dilute phase section 13 extends into the reaction disengager 3. A few layers of gratings 10 are arranged within the dense phase section 1.

A cyclone quick separation assembly 6' is arranged within the reaction disengager 3, the cyclone quick separation assembly 6' includes a first flow divider 61', and a second flow divider 62' and further includes a third flow divider 63'. The first, second and third flow dividers are located above the outlet of the reactor.

The cyclone quick separation assembly may also achieve the effect of quick separation of the oil gas and catalyst in the present disclosure when the cyclone quick separation assembly includes the first flow divider 61' and the second flow divider 62'. In the case where the third flow divider 63' is included, a better separation effect is achieved.

The first flow divider 61' may be a conical first cover body as shown in FIG. 8A or a spherical crown shaped first cover body as shown in FIG. 8B, and may also be a first cover body with a structure shown in FIG. 8C. The first flow divider 61' shown in FIG. 8C is composed of two parts, an upper part has a conical structure and a lower part is a first cover body which is gradually expanded in diameter from bottom to top. And the edge of the longitudinal section of the first cover passing through the center line is two curves passing through the apex and bending away from the center, and the curvature of each curve first increases and then decreases from bottom to top. The lowermost bottom edge of the conical structure of the upper part is connected with the uppermost periphery of the lower part. The upper and lower parts may also be integrally formed.

As shown in FIGS. 8A, 8B, and 8C, the second flow divider 62' includes a truncated cone-shaped structure and a flow diversion pipe 621 connected with the smallest cross section of the truncated cone-shaped structure or integrally formed with the circular truncated cone-shaped structure to form the second flow divider 62'. The first flow divider 61' is located inside the second flow divider 62'.

The third flow divider 63' is shaped similarly to the first flow divider 61'. The shape of the first flow divider and the shape of the third flow divider may be the same or different. For example, the first flow divider 61' may have a spherical crown structure and the third flow divider 63' may have a conical structure.

The angle between the generatrix and the lower bottom surface of the cone of each of the first flow divider and the third flow divider (61' and 63') is greater than the angle of repose of the catalyst particles. That is, the magnitude of the angle of the cone is related to the angle of repose of the catalyst particles used, so that a downward flow of the catalyst can be ensured.

The area of the cross section of the lowermost end (i.e. the end closest to the outlet of the reactor) of the first flow divider 61' is greater than or equal to the cross-sectional area of the outlet of the dilute phase section 13 of the reactor if the first flow divider 61' is a first cover body of a conical structure or spherical crown structure. Preferably, the area of the cross section of the lowermost end of the first flow divider is greater than the cross-sectional area of the outlet of the dilute phase section 13 of the reactor and less than 2 times of the cross-sectional area of the dilute phase section 13 of the reactor.

When the first flow divider 61' has a structure as shown in FIG. 8C, the cross-sectional area of the lowermost end of the conical structure of its upper part is greater than the cross-sectional area of the outlet of the dilute phase section 13 of the reactor and less than 2 times of the cross-sectional area of the dilute phase section 13 of the reactor.

In this embodiment, the lowermost end of the first flow divider 61' is higher than the outlet of the dilute phase section 13 of the reactor. The cross-sectional area of the annular gap formed between the outlet of the dilute phase section 13 of the reactor and the lower edge of the first flow divider 61' is less than or equal to the cross-sectional area of the outlet of the dilute phase section 13 of the reactor.

Figure 9:
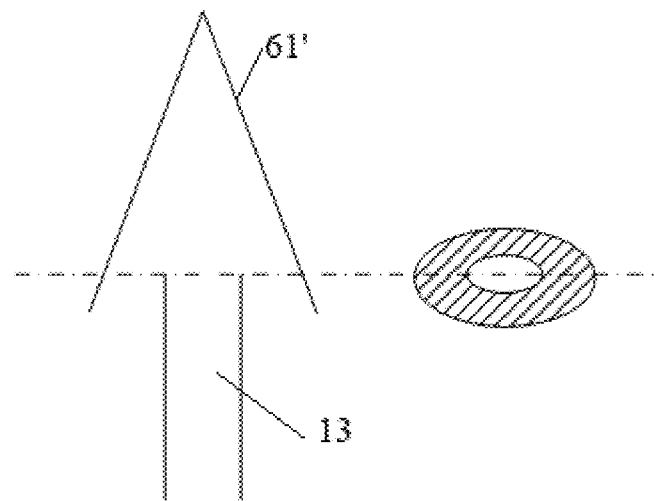
FIG. 9 is a cross-sectional view of another quick separation assembly of the present disclosure.

It is also possible that the lowermost end of the first flow divider 61' is lower than the outlet of the dilute phase section 13 of the reactor, as shown in FIG. 9, the cross-sectional area (a shaded part of FIG. 9) of the annular gap formed between the outlet of the dilute phase section 13 of the reactor and the first flow divider is less than or equal to the cross-sectional area of the outlet of the dilute phase section 13 of the reactor.

In this embodiment, the maximum cross-sectional area of the truncated cone-shaped structure of the second flow divider 62' is greater than 1.5 times of the cross-sectional area of the lowermost end of the first flow divider 61'. The minimum spacing of the gap between the first flow divider 61' and the second flow divider 62' should be greater than the cross-sectional diameter of the outlet of the dilute phase section 13 of the reactor.

In this embodiment, the cross-sectional area of the lowermost end of the third flow divider 63' is greater than or equal to the cross-sectional area of the outlet of the flow diversion pipe 621 in the second flow divider 62'. The lowermost end of the third flow divider is higher than the position of the outlet of the flow diversion pipe of the second flow divider. Preferably, the cross-sectional area of the annular gap between the outlet of the flow diversion pipe and the lower edge of the third flow divider is greater than or equal to the cross-sectional area of the outlet of the flow diversion pipe.

In this embodiment, in the reaction disengager 3, a cyclone separator 8 is arranged outside the cyclone quick separation assembly 6', the cyclone separator includes at least two first-stage cyclone separators 81 and at least two second-stage cyclone separators 82, and the second-stage cyclone separators is communicated with the gas collecting chamber 20 through risers. The inlets of the first-stage cyclone separators 81 are in the same horizontal plane as the inlet of the flow diversion pipe 621 of the second flow divider 62', or the inlets of the first-stage cyclone separators 81 are slightly lower than the inlet of the flow diversion pipe 621. As shown in FIG. 11, in the catalyst entrained gas flowing upwards in the flow diversion pipe 621 of the second flow divider 62', under the action of the third flow divider 63', one part of the catalyst directly settles and falls and another part of the catalyst flows out from the lower part of the third flow divider, the gas generally flows horizontally or obliquely downward towards the inlet of the cyclone separator and the catalyst naturally settles in the absence of upward force.

Figure 10:
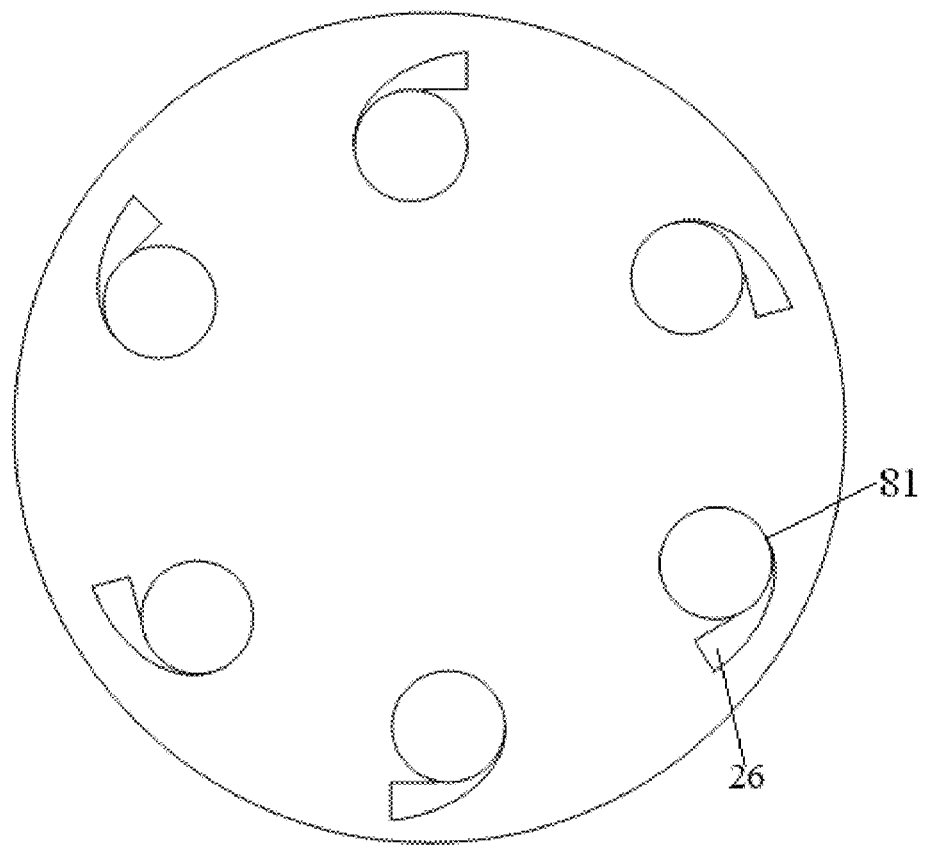
FIG. 10 is a top view within the disengager of the present disclosure.

As shown in FIG. 10, the plurality of cyclone separators are arranged uniformly along the circumferential direction of the disengager 3 and the inlets of the first-stage cyclone separators 81 are arranged close to the wall of the disengager 3 and the inlets 26 of all cyclone separators 81 are arranged circumferentially towards the counterclockwise direction.

The cyclone quick separation device 6' within the disengager of the reaction device may also be disposed within the disengager 3 of the regeneration device.

EMBODIMENT 4

Figure 12:
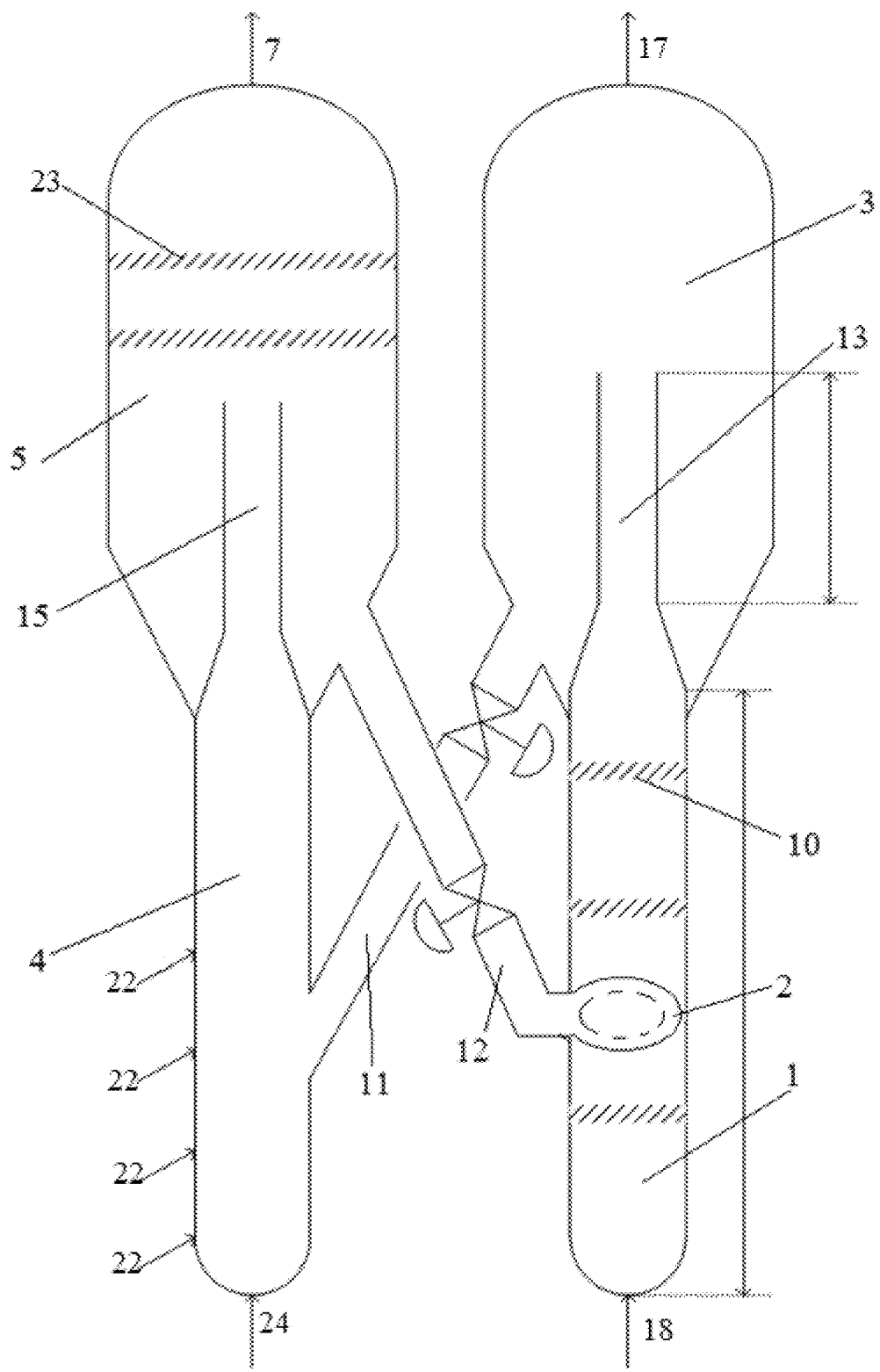
FIG. 12 shows a regeneration device for the catalytic dehydrogenation of alkanes of the present disclosure.

According to the circulating fluidized bed alkane catalytic dehydrogenation reaction-regeneration device of this embodiment, the reaction device and the regeneration device are arranged in parallel, with reference to FIG. 12.

The regeneration device for an alkane catalytic dehydrogenation catalyst includes a regenerator accommodating a catalyst and a regeneration disengager section 5, and both the regenerator and the regeneration disengager section are tanks. The regeneration disengager section 5 is located above the regenerator, the regenerator includes a dense phase section 4 and a dilute phase section 15. And the pipe wall of the dense phase section 4 is provided with four fuel nozzles 22 along the axial direction. The nozzles 22 are equidistant, and the highest fuel nozzle is arranged at a distance of ½-⅔ of the total height of the dense phase section of the regenerator from the bottom of the regenerator. The bottom of the dense phase section 4 is provided with an air inlet and the fuel nozzles 22.

Two layers of high-temperature-resistant stainless steel meshes 23 are arranged in the regeneration disengager 5.

The reaction device for the catalytic dehydrogenation of alkanes includes a reactor and a reaction disengager 3 located at the upper part of the reactor, the reactor includes a catalyst distributor 2, a dense phase section 1 and a dilute phase section 13. Both the dense phase section 1 and the dilute phase section 13 are of equal diameter structures and the dilute phase section 13 extends into the reaction disengager 3. The catalyst distributor 2 is located between ⅙ and ⅚, preferably ½ and ⅔ of the height of the dense phase section 1 of the reactor, based on the bottom of the reactor, and the catalyst distributor 2 is arranged above the alkane dehydrogenation feedstock inlet.

A few layers of gratings 10 are arranged in the dense phase section 1 of the reactor.

In experimental examples 2-5, the reaction is carried out by using the alkane catalytic dehydrogenation reaction-regeneration device provided in Embodiment 1 of the present disclosure, and the specific reaction process and reaction results are shown in experimental examples 2-5. In experimental example 1, a catalyst feeding annular pipe of the present disclosure is not used.

The catalyst ADHO-1 used in experimental examples 1-5 is an alkane dehydrogenation catalyst in the inventor's patent ZL201110123675.1. The catalyst carrier is alumina, and a catalyst prepared from zinc oxide, tungsten oxide and sodium oxide is also included. The mass ratio of zinc oxide to tungsten oxide is about 8.4, and the content of sodium oxide is appropriate.

EXPERIMENTAL EXAMPLE 1

Dehydrogenation of Propane to Propylene

Feedstock: 99.9 wt % of propane

Catalyst: environmental-friendly metal oxide catalyst ADHO-1 (ZL201110123675.1)

Mean bed temperature: 600° C.

Reaction-regeneration system structural form: the regenerated catalyst enters the reactor from the side of the reactor at a location that is ½ of the height of the dense phase section of the reactor, based on the bottom of the reactor. The regeneration sloped pipe ends at an opening in the side of the reactor.

EXPERIMENTAL EXAMPLE 2

Dehydrogenation of Propane to Propylene

Feedstock: 99.9 wt % of propane
Catalyst: environmental-friendly metal oxide catalyst ADHO-1 (ZL201110123675.1)
Mean bed temperature: 600° C.
Reaction-regeneration system structural form: the regenerated catalyst enters the reactor from the side of the reactor at a location that is ½ of the height of the dense phase section of the reactor, based on the bottom of the reactor. The regeneration sloped pipe is connected with a catalyst distribution pipe with a plurality of openings in a circular side, and the positions of the openings in the catalyst distribution annular pipe are shown in FIG. 1.

EXPERIMENTAL EXAMPLE 3

Dehydrogenation of Propane to Propylene

Feedstock: 99.9 wt % of propane
Catalyst: environmental-friendly metal oxide catalyst ADHO-1 (ZL201110123675.1)
Mean bed temperature: 600° C.
Reaction-regeneration system structural form: the regenerated catalyst enters the reactor from the side of the reactor at a location that is ⅔ of the height of the dense phase section of the reactor, based on the bottom of the reactor. The regeneration sloped pipe is connected with a catalyst distribution pipe with a plurality of openings in a circular side, and the positions of the openings in the catalyst distribution annular pipe are shown in FIG. 1.

TABLE 1

Propane dehydrogenation product distribution and propylene selectivity, wt % in experimental examples 1-3

| Composition | Experimental example 1 | | Experimental example 2 | | Experimental example 3 | |
| --- | --- | --- | --- | --- | --- | --- |
| | Product distribution | Selectivity | Product distribution | Selectivity | Product distribution | Selectivity |
| $H_2$ | 1.5 | 4.31 | 1.61 | 4.39 | 1.66 | 4.16 |
| $CH_4$ | 1.98 | 5.69 | 1.64 | 4.47 | 1.42 | 3.56 |
| $C_2H_6$ | 1.63 | 4.69 | 1.02 | 2.78 | 0.93 | 2.33 |
| $C_2H_4$ | 0.78 | 2.24 | 0.51 | 1.39 | 0.61 | 1.53 |
| $C_3H_8$ | 65.22 | | 63.34 | | 60.12 | |
| $C_3H_6$ | 26.91 | 77.37 | 30.62 | 83.52 | 34.17 | 85.68 |
| $C_4H_8$ | 0.72 | 2.07 | 0.41 | 1.12 | 0.43 | 1.08 |
| C5+ | 0.32 | 0.92 | 0.21 | 0.57 | 0 | 0.00 |
| Coke | 0.94 | 2.71 | 0.64 | 1.75 | 0.66 | 1.65 |

EXPERIMENTAL EXAMPLE 4

Dehydrogenation of Isobutane to Isobutylene

Feedstock: 99.9 wt % of isobutane
Catalyst: environmental-friendly metal oxide catalyst ADHO-1 (ZL201110123675.1)
Mean bed temperature: 580° C.
Reaction-regeneration system structural form: a regenerant enters the reactor from the side of the reactor at a location that is ½ of the height of the dense phase section of the reactor, based on the bottom of the reactor. The regeneration sloped pipe is connected with a catalyst distribution pipe with a plurality of openings in a circular side, and the positions of the openings in the catalyst distribution annular pipe are shown in FIG. 1.

EXPERIMENTAL EXAMPLE 5

Dehydrogenation of Isobutane to Isobutylene

Feedstock: 99.9 wt % of isobutane
Catalyst: environmental-friendly metal oxide catalyst ADHO-1 (ZL201110123675.1)
Mean bed temperature: 580° C.
Reaction-regeneration system structural form: a regenerant enters the reactor from the side of the reactor at a location that is ⅔ of the height of the dense phase section of the reactor, based on the bottom of the reactor. The regeneration sloped pipe is connected to a catalyst distribution pipe with a plurality of openings in a circular side, and the positions of the openings in the catalyst distribution annular pipe are shown in FIG. 1.

TABLE 2

Isobutane dehydrogenation product distribution and isobutylene selectivity, wt % in experimental examples 4-5

| Composition | Experimental example 4 | | Experimental example 5 | |
| --- | --- | --- | --- | --- |
| | Product distribution | Selectivity | Product distribution | Selectivity |
| $H_2$ | 1.61 | 3.23 | 1.59 | 2.96 |
| $CH_4$ | 1.94 | 3.70 | 1.61 | 2.81 |
| $C_2H_6$ | 0.36 | 0.72 | 0.23 | 0.43 |
| $C_2H_4$ | 0.45 | 0.90 | 0.41 | 0.76 |
| $C_3H_8$ | 1.51 | 3.03 | 1.02 | 1.90 |
| $C_3H_6$ | 1.42 | 2.85 | 0.88 | 1.64 |
| $i\text{-}C_4H_{10}$ | 50.11 | — | 46.11 | |
| $n\text{-}C_4H_{10}$ | 0.06 | 0.12 | 0.04 | 0.07 |

TABLE 2-continued

Isobutane dehydrogenation product distribution and
isobutylene selectivity, wt % in experimental examples 4-5

| | Experimental example 4 | | Experimental example 5 | |
|---|---|---|---|---|
| Composition | Product distribution | Selectivity | Product distribution | Selectivity |
| n-$C_4H_8$ | 0.56 | 1.12 | 0.36 | 0.67 |
| i-$C_4H_8$ | 40.13 | 80.60 | 45.95 | 85.42 |
| C5+ | 0.61 | 1.23 | 0.61 | 1.13 |
| Coke | 1.24 | 2.49 | 1.19 | 2.21 |

The following is a dehydrogenation reaction carried out by using the reaction device for catalytic dehydrogenation of alkanes provided in Embodiment 2 of the present disclosure, and the specific reaction process and reaction results are shown in experimental example 7.

The reaction conditions for experimental examples 6-7 are as follows:
Other reaction conditions, feedstock: 99.9 wt % of propane
Catalyst: an alkane dehydrogenation catalyst in the patent ZL201110123675.1 is used, the catalyst carrier is alumina, and a catalyst prepared from zinc oxide, tungsten oxide and sodium oxide is also included. The mass ratio of zinc oxide to tungsten oxide is about 8.4 and the content of sodium oxide is appropriate.
Mean bed temperature: 600° C.

EXPERIMENTAL EXAMPLE 6

Experimental example 1: the linear velocity of the outlet of the dilute phase transport pipe is 10 m/s, a simple hemispherical barrier is arranged inside the reaction disengager, and a cross-sectional area of the lower edge of the barrier is 3 times of a cross-sectional area of the outlet of the dilute phase transport pipe. The barrier is at a distance of 2 m from the interface of the dilute phase and the dense phase, and the vertical distance between the barrier and the outlet of the dilute phase transport pipe of the reactor is ½ of the hemisphere radius. The superficial gas velocity inside the disengager is 0.6 m/s. The catalyst concentration (which may also be referred to as the fluidization density of the catalyst) at the outlet of the dilute phase transport pipe is measured to be 40 kg/$m^3$, the catalyst concentration at the inlet of the cyclone separator is 10 kg/$m^3$, and the gas-solid separation efficiency of the structure is 75%. The pressure drop of this structure is 1.3 kPa.

EXPERIMENTAL EXAMPLE 7

The alkane dehydrogenation reaction is performed by using the reaction device of Embodiment 2 in this experimental example. The angle between the generatrix of and the bottom surface of the circular truncated cone part of the cover body is 45°, the area of the bottom surface is the same as the cylindrical cross-sectional area of the lower part of Embodiment 2, and the vertical distance between the lower edge of the cover body and the outlet of the dilute phase delivery pipe is half the radius of the cylindrical structure of the cover body. Half of the total gas volume passes through the primary cyclone separator, with an inlet linear velocity of 5 m/s. The catalyst concentration at the outlet of the dilute phase delivery pipe is still 40 kg/$m^3$ and the catalyst concentration at the inlet of the first-stage cyclone separator is 3 kg/$m^3$ and the gas-solid separation efficiency of this structure is 92.5%. The pressure drop of this structure is less than 1 kPa.

The following is a dehydrogenation reaction carried out by using the reaction device for catalytic dehydrogenation of alkanes provided in Embodiment 3 of the present disclosure, and the specific reaction process and reaction results are shown in experimental example 9.

The reaction conditions of experimental examples 8-9 are as follows:
Other reaction conditions, feedstock: 99.9 wt % of propane
Catalyst: an alkane dehydrogenation catalyst in the patent ZL201110123675.1 is used, the catalyst carrier is alumina, and a catalyst prepared from zinc oxide, tungsten oxide and sodium oxide is also included. The mass ratio of zinc oxide to tungsten oxide is about 8.4 and the content of sodium oxide is appropriate.
Mean bed temperature: 600° C.

EXPERIMENTAL EXAMPLE 8

Other structural references for other reaction devices are shown in FIG. 1 except that the quick separation assembly is different. The reaction device of this experimental example is provided with a conical flow divider above the outlet of the dilute phase transport pipe within the disengager, as shown in FIG. 9, the cross-sectional area of the lower end of the flow divider is 3 times of the cross-sectional area of the outlet of the dilute phase transport pipe, the angle between the generatrix and the bottom surface of the cone of the flow divider is 60°. And the area of the annular gap between the flow divider and the position of the outlet of the dilute phase transport pipe is 1.5 times of the area of the outlet of the dilute phase transport pipe. The lower end of the flow divider is located within the dense phase section of the disengager, and the lower end of the flow divider is 2 m from the interface of the dilute phase and the dense phase within the disengager. The linear velocity of the outlet of the dilute phase transport pipe of the reactor is 10 m/s and the superficial gas velocity inside the disengager is 0.6 m/s. The catalyst concentration (which may also be referred to as the fluidization density of the catalyst) at the outlet of the dilute phase delivery pipe is measured to be 42 kg/$m^3$, the catalyst concentration at the inlet of the cyclone separator is 9.8 kg/$m^3$, and the gas-solid separation efficiency of this structure is 77%. The pressure drop of this structure is 1.15 kPa.

EXPERIMENTAL EXAMPLE 9

Other conditions are unchanged and the cyclone quick separation assembly in this experimental example employs a composite flow divider as shown in FIG. 1. As shown in FIGS. 8A-8C, the angle between the generatrix and the bottom surface of the cone of each of the first, second and third flow dividers is 60°. The bottom surface of the first flow divider is higher than the outlet of the dilute phase transport pipe. The area of the annular gap formed by the position of the annular gap area (fluid flow area) between the first flow divider and the outlet of the dilute phase delivery pipe is 2.5 times of the area of the outlet of the dilute phase delivery pipe. The bottom area of the second flow divider is 3 times of the cross-sectional area of the outlet of the dilute phase transport pipe. The distance between the first flow divider and the second flow divider is 1.2 times of the outlet diameter of the dilute phase transport pipe. The outlet area at the top of the second flow divider is equal to the area of the outlet of the dilute phase transport pipe, and the bottom area of the third flow divider is the same as that of the first flow divider. The catalyst concentration at the outlet of the dilute phase delivery pipe is still 42 kg/m³. The catalyst concentration at the inlet of the cyclone separator is 2.8 kg/m³, and the gas-solid separation efficiency of this structure is 93.3%. The pressure drop of this structure is less than 0.7 kPa.

Experimental examples 10-12 further illustrate the effect of the regeneration process for the alkane catalytic dehydrogenation catalyst of the present disclosure in combination with Embodiment 5:

EXPERIMENTAL EXAMPLE 10

With natural gas as fuel, the air-fuel ratio is set according to the complete combustion of natural gas to generate carbon dioxide and water. The catalyst settled down in the regenerator disengager section has a temperature of 750° C. Fuel is sprayed into the regenerator through 5 equidistant nozzles, a mass ratio of the sprayed fuel is 5:4:3:2:1 from bottom to top. No stainless steel mesh or grating is arranged inside the regenerator disengager section, and the spent catalyst and the catalyst returned from the catalyst external circulation pipe are all above the main air (air) distribution pipe at the bottom of the regenerator. The temperature of the spent catalyst returned to the regenerator is 556° C. The temperatures of the five temperature measurement points at different axial positions of the regenerator are 718° C., 757° C., 769° C., 782° C. and 775° C., respectively, and the concentration of NOx in the flue gas is 94 mg/m³. The introduction of fuel in different axial positions can not only avoid the generation of hot spots, but also help to reduce the concentration of NOx in flue gas.

EXPERIMENTAL EXAMPLE 11

Others are the same as Experimental example 10. The difference from Experimental example 10 is that two layers of stainless steel gratings are arranged within the regenerator disengager section and the concentration of NOx in the flue gas is measured to be 36 mg/m³. Obviously, the stainless steel gratings can catalyze the reduction of NOx.

EXPERIMENTAL EXAMPLE 12

With natural gas as fuel, the air-fuel ratio is set according to the complete combustion of natural gas to generate carbon dioxide and water, the temperature of the catalyst settled down in the regenerator disengager section is 750° C. All fuel enter the bottom of the regenerator, no stainless steel mesh or grating is arranged inside the regenerator disengager section, and the spent catalyst and the catalyst returned from the catalyst external circulation pipe are all above the main air (air) distribution pipe at the bottom of the regenerator. The temperature of the spent catalyst returned to the regenerator is 556° C. The temperatures of the five temperature measurement points at different axial positions of the regenerator are 830° C., 812° C., 793° C., 786° C. and 774° C., respectively, and the concentration of NOx in the flue gas is 144 mg/m³. When fuel and air enter the regenerator at the same axial position, there is a phenomenon of rapid concentrated combustion of fuel, which will produce hot spots.

The present disclosure is described in detail for the purpose of enabling those skilled in the art to understand and practice the contents of the present disclosure, and is not intended to limit the scope of the present disclosure. All equivalent changes or modifications made in accordance with the spirit of the present disclosure should be covered within the scope of protection of the present disclosure.

The invention claimed is:
1. An alkane dehydrogenation circulating fluidized bed device, comprising a reaction device,
  wherein the reaction device comprises a reactor and a reaction disengager, the reaction disengager is communicated with the reactor, a reaction feedstock inlet is arranged on the reactor,
  wherein a catalyst distributor is arranged in the reactor so that a catalyst is sprayed into the reactor along a direction from a peripheral wall of the reactor to a center axis of the reactor through the catalyst distributor, and the reaction feedstock inlet is located below the catalyst distributor;
  wherein, a primary cyclone separator, a primary cyclone riser and a cover body are arranged in the reaction disengager;
  the cover body comprises an upper part and a lower part, the upper part of the cover body is a truncated cone, and the lower part of the cover body is below a lower base of the truncated cone; an area of an opening in a lowermost end of the cover body is greater than an area of an outlet of the reactor;
  a circumference of an upper base of the truncated cone is connected with a periphery of the primary cyclone riser, or the circumference of the upper base of the truncated cone is connected with a periphery of the primary cyclone separator above an inlet of the primary cyclone separator; and
  a part or whole of the primary cyclone separator is located in the cover body.
2. The alkane dehydrogenation circulating fluidized bed device according to claim 1, wherein the catalyst distributor is an annular pipe, a center axis of the annular pipe is parallel to the center axis of the reactor, and an opening is arranged on the annular pipe for allowing the catalyst to be sprayed towards the center axis of the annular pipe.
3. The alkane dehydrogenation circulating fluidized bed device according to claim 2, wherein the opening on the annular pipe is located at a wall close to the center axis of the annular pipe.
4. The alkane dehydrogenation circulating fluidized bed device according to claim 2, wherein a through opening is arranged on a wall of the annular pipe close to and around the center axis of the annular pipe; or
  two or more openings are arranged on the wall close to the center axis of the annular pipe along a circumferential direction and are evenly distributed.
5. The alkane dehydrogenation circulating fluidized bed device according to claim 2, wherein based on a plane of a wall of the annular pipe closest to the center axis of the annular pipe, the opening for allowing the catalyst to be sprayed is arranged on the wall of the annular pipe on the plane, and a direction of the opening is toward the center axis of the annular pipe.
6. The alkane dehydrogenation circulating fluidized bed device according to claim 1, wherein the catalyst distributor is an annular pipe, a center axis of the annular pipe is parallel to the center axis of the reactor, and nozzles are arranged on a wall, close to the center axis, of the annular pipe; the catalyst is configured to be sprayed through the nozzles;
  the nozzles are evenly arranged on the wall, close to the center axis, of the annular pipe, opening directions of the nozzles are perpendicular to the center axis of the annular pipe, or the opening directions of the nozzles are sloped upwards.

7. The alkane dehydrogenation circulating fluidized bed device according to claim 1, wherein the primary cyclone separator comprises a primary cyclone separator body and a conveying part, the conveying part is located under the primary cyclone separator body, an edge of the upper base of the truncated cone of the cover body is connected with the periphery of the primary cyclone separator above the inlet of the primary cyclone separator.

8. The alkane dehydrogenation circulating fluidized bed device according to claim 1, wherein the primary cyclone riser is arranged at a top of the primary cyclone separator and communicated with the primary cyclone separator, and the edge of the upper base of the truncated cone of the cover body is connected with the periphery of the primary cyclone riser.

9. The alkane dehydrogenation circulating fluidized bed device according to claim 8, wherein within the reaction disengager, the lowermost end of the cover body is lower than the outlet of the reactor.

10. The alkane dehydrogenation circulating fluidized bed device according to claim 1, wherein the area of the opening in the lowermost end of the cover body is greater than or equal to the area of the outlet of the reactor;
the area of the opening in the lowermost end of the cover body is 1.5-5 times the area of the outlet of the reactor.

11. The alkane dehydrogenation circulating fluidized bed device according to claim 1, wherein an additional cyclone separator is arranged outside the cover body in the reaction disengager, and there is a gap between an outlet of the primary cyclone riser and an inlet of the additional cyclone separator.

12. An alkane dehydrogenation circulating fluidized bed device, comprising a reaction device,
wherein the reaction device comprises a reactor and a reaction disengager, the reaction disengager is communicated with the reactor, a reaction feedstock inlet is arranged on the reactor,
wherein a catalyst distributor is arranged in the reactor so that a catalyst is sprayed into the reactor along a direction from a peripheral wall of the reactor to a center axis of the reactor through the catalyst distributor, and the reaction feedstock inlet is located below the catalyst distributor,
wherein an outlet of the reactor is located in the reaction disengager, the reaction disengager is provided with a first flow divider and a second flow divider, and both the first flow divider and the second flow divider are located above the outlet of the reactor;
the first flow divider is configured to reduce a gas velocity in an upward direction of a gas flow discharged from the outlet of the reactor,
the second flow divider comprises a second cover body with openings in both upper and lower ends, a cross-sectional area of the opening in the lower end is greater than a cross-sectional area of the opening in the upper end, and the first flow divider is located in the second flow divider.

13. The alkane dehydrogenation circulating fluidized bed device according to claim 12, wherein the first flow divider is a first cover body, a cross-sectional area of the first cover body gradually decreases from bottom to top, and the first cover body has an opening only in a lowest end.

14. The alkane dehydrogenation circulating fluidized bed device according to claim 13, wherein a minimum spacing of a gap between the first flow divider and the second flow divider is greater than a cross-sectional diameter of the outlet of the reactor.

15. The alkane dehydrogenation circulating fluidized bed device according to claim 12, wherein the first flow divider comprises a first cover body having a conical structure with cross-sectional area gradually increasing from bottom to top, edges of a section of the first cover passing through a cone apex in a longitudinal direction are present by two curves passing through the cone apex, and a curvature of each curve firstly increases, and then decreases from the cone apex to a base edge of the conical structure;
the first flow divider further comprises a cavity having a conical structure with cross-sectional area gradually increasing from top to bottom; an end, near the outlet of the reactor, of the cavity is a base of the cavity; an end, away from the outlet of the reactor, of the first cover body is a base of the first cover body, and the base of the first cover body is connected with the base of the cavity.

16. The alkane dehydrogenation circulating fluidized bed device according to claim 12, wherein the second flow divider further comprises a flow diversion pipe, and an end of the flow diversion pipe is connected with the upper opening in the lower end of the second cover body.

17. The alkane dehydrogenation circulating fluidized bed device according to claim 16, wherein a cross-sectional area of the lower end of the second flow divider is greater than 1.5 times of a cross-sectional area of a lower end of the first flow divider.

18. The alkane dehydrogenation circulating fluidized bed device according to claim 12, wherein a third flow divider is arranged in the reaction disengager, the third flow divider is located above the second flow divider, the third flow divider is a third cover body with the cross-sectional area gradually decreasing from bottom to top, and the third cover body has an opening only in a lower end.

19. The alkane dehydrogenation circulating fluidized bed device according to claim 18, wherein the cross-sectional area of the lower end of the third flow divider is greater than or equal to the cross-sectional area of the opening in the upper end of the second flow divider;
the lower end of the third flow divider is lower than an outlet of a flow diversion pipe of the second flow divider; a cross-sectional area of an annular gap formed between the outlet of the flow diversion pipe and the third flow divider is greater than or equal to a cross-sectional area of the outlet of the flow diversion pipe;
or, the lower end of the third flow divider is higher than the outlet of the flow diversion pipe of the second flow divider; a cross-sectional area of an annular gap formed between the outlet of the flow diversion pipe and a lower end of the third flow divider is greater than or equal to the cross-sectional area of the outlet of the flow diversion pipe.

* * * * *